(12) United States Patent
Verleur et al.

(10) Patent No.: US 10,085,481 B2
(45) Date of Patent: Oct. 2, 2018

(54) VAPORIZER

(71) Applicant: VMR Products, LLC, Miami, FL (US)

(72) Inventors: Jan Andries Verleur, Miami Beach, FL (US); Dan Recio, Miami, FL (US); Yifeng Lu, Miami, FL (US); Yinjun Zhang, Miami, FL (US); Arturo Fajardo, Miami, FL (US); Hans Verleur, El Dorado, CA (US)

(73) Assignee: VMR Products, LLC, Miami, FL (US)

( * ) Notice: Subject to any disclaimer, the term of this patent is extended or adjusted under 35 U.S.C. 154(b) by 324 days.

(21) Appl. No.: 14/539,801

(22) Filed: Nov. 12, 2014

(65) Prior Publication Data

US 2015/0128976 A1 May 14, 2015

Related U.S. Application Data

(60) Provisional application No. 61/903,344, filed on Nov. 12, 2013, provisional application No. 61/937,851, (Continued)

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .............................. A24F 47/008; A61M 15/06
(Continued)

(56) References Cited

U.S. PATENT DOCUMENTS

| 1,446,087 A | 2/1923 | Griffin |
| 2,057,353 A | 10/1936 | Whittemore, Jr. |

(Continued)

FOREIGN PATENT DOCUMENTS

| CA | 2 846 286 A1 | 4/2013 |
| CN | 1233436 A | 11/1999 |

(Continued)

OTHER PUBLICATIONS

European Patent Office, Partial European Search Report dated Oct. 13, 2015 for EP Application No. 14159709.6 filed Mar. 14, 2014.

(Continued)

*Primary Examiner* — Joseph S Del Sole
*Assistant Examiner* — Mohamed K Ahmed Ali
(74) *Attorney, Agent, or Firm* — Hillyer Legal

(57) ABSTRACT

An electronic cigarette or vaporizer may include a shell and a cartomizer receivable within a chamber within a portion of the shell. The cartomizer may hold a vaporizable fluid, dry substance, or other vaporizable substance such as a wax. A charger may also be included which in one embodiment may be insertable into the chamber, and in another embodiment may be connectable to an end of the shell. Various electrical components, such as a printed circuit board, a recharagable battery, various indicator lights, a sensor, and display screen, for instance, improve the functionality of the vaporizer from known vaporizers. Magnets may also be provided in order to secure the cartomizer or the charger to the shell.

12 Claims, 19 Drawing Sheets

Related U.S. Application Data filed on Feb. 10, 2014, provisional application No. 62/015,148, filed on Jun. 20, 2014.

(51) Int. Cl.
*A61M 11/04* (2006.01)
*H02J 7/00* (2006.01)

(52) U.S. Cl.
CPC .......... *H02J 7/0042* (2013.01); *H02J 7/0052* (2013.01); *A61M 2205/332* (2013.01); *A61M 2205/3368* (2013.01); *A61M 2205/502* (2013.01); *A61M 2205/584* (2013.01); *A61M 2205/8206* (2013.01); *A61M 2205/8237* (2013.01)

(58) Field of Classification Search
USPC ........................................................ 131/329
See application file for complete search history.

(56) References Cited

U.S. PATENT DOCUMENTS

| | | |
|---|---|---|
| 2,545,851 A | 3/1951 | Kardos |
| 3,060,429 A | 10/1962 | Winston |
| 3,200,819 A | 8/1965 | Gilbert |
| 3,203,025 A | 8/1965 | Schreur |
| 3,400,998 A | 9/1968 | Daugherty et al. |
| 3,479,561 A | 11/1969 | Janning |
| 3,502,588 A | 3/1970 | Winberg |
| 3,521,216 A | 7/1970 | Tolegian |
| 3,747,120 A | 7/1973 | Stemme |
| D248,047 S | 5/1978 | Rappoport |
| D251,072 S | 2/1979 | Stuetzer |
| 4,207,457 A | 6/1980 | Haglund et al. |
| D257,519 S | 11/1980 | Plozner |
| D259,588 S | 6/1981 | Stutzer |
| D260,690 S | 9/1981 | Stutzer |
| D260,941 S | 9/1981 | Figur |
| 4,569,136 A | 2/1986 | Loring |
| 4,676,237 A | 6/1987 | Wood et al. |
| 4,771,295 A | 9/1988 | Baker et al. |
| 4,771,796 A | 9/1988 | Myer |
| 4,797,692 A | 1/1989 | Ims |
| 4,848,374 A | 7/1989 | Chard et al. |
| 4,945,448 A | 8/1990 | Bremenour et al. |
| 4,945,929 A | 8/1990 | Egilmex |
| 4,972,855 A | 11/1990 | Kuriyama et al. |
| 4,990,939 A | 2/1991 | Sekiya et al. |
| 5,060,671 A | 10/1991 | Counts et al. |
| 5,124,200 A | 6/1992 | Mallonee |
| 5,144,962 A | 9/1992 | Counts et al. |
| 5,224,265 A | 7/1993 | Dux et al. |
| 5,269,327 A | 12/1993 | Counts et al. |
| 5,327,915 A | 7/1994 | Porenski et al. |
| 5,388,574 A | 2/1995 | Ingebrethsen |
| 5,505,214 A | 4/1996 | Collins et al. |
| 5,646,666 A | 7/1997 | Cowger et al. |
| 5,666,977 A | 9/1997 | Higgins et al. |
| 5,703,633 A | 12/1997 | Gehrer et al. |
| 5,743,251 A | 4/1998 | Howell et al. |
| 5,819,756 A | 10/1998 | Mielordt |
| 5,894,841 A | 4/1999 | Voges |
| 5,996,589 A | 12/1999 | St. Charles |
| 6,062,213 A | 5/2000 | Fuisz et al. |
| 6,155,268 A | 12/2000 | Takeuchi |
| 6,196,218 B1 | 3/2001 | Voges |
| 6,234,167 B1 | 5/2001 | Cox et al. |
| 6,322,268 B1 | 11/2001 | Kaufmann et al. |
| 6,471,782 B1 | 10/2002 | Fang et al. |
| 6,501,052 B2 | 12/2002 | Cox et al. |
| 6,598,607 B2 | 7/2003 | Adiga et al. |
| 6,620,659 B2 | 9/2003 | Emma et al. |
| 6,701,921 B2 | 3/2004 | Sprinkel, Jr. et al. |
| 6,719,443 B2 | 4/2004 | Gutstein et al. |
| 6,722,763 B1 | 4/2004 | Hsu et al. |
| 7,059,307 B2 | 6/2006 | Pellizzari et al. |
| D531,180 S | 10/2006 | Goto |
| 7,143,766 B2 | 12/2006 | Schuster et al. |
| D624,238 S | 9/2010 | Turner |
| D642,330 S | 7/2011 | Turner |
| D644,375 S | 8/2011 | Zhou |
| D645,816 S | 9/2011 | Sasada et al. |
| D675,777 S | 2/2013 | Wu |
| 8,365,742 B2 | 2/2013 | Hon |
| 8,375,957 B2 | 2/2013 | Hon |
| 8,393,331 B2 | 3/2013 | Hon |
| 8,490,628 B2 | 7/2013 | Hon |
| D688,415 S | 8/2013 | Kim |
| D693,053 S | 11/2013 | Chen |
| D693,765 S | 11/2013 | Workman et al. |
| D695,450 S | 12/2013 | Benassayag et al. |
| D702,876 S | 4/2014 | Liu |
| D704,634 S | 5/2014 | Eidelman et al. |
| D718,492 S | 11/2014 | Albanese |
| 8,893,726 B2 | 11/2014 | Hon |
| D720,094 S | 12/2014 | Alima |
| D720,095 S | 12/2014 | Alima |
| D720,496 S | 12/2014 | Alima |
| D720,497 S | 12/2014 | Alima |
| D720,881 S | 1/2015 | Liu |
| D720,882 S | 1/2015 | Albanese |
| D720,883 S | 1/2015 | Albanese |
| D721,202 S | 1/2015 | Liu |
| D722,166 S | 2/2015 | Buehl et al. |
| D722,956 S | 2/2015 | Alima |
| 8,955,522 B1 | 2/2015 | Bowen et al. |
| D724,263 S | 3/2015 | Malhi |
| D724,782 S | 3/2015 | Wu |
| D725,310 S | 3/2015 | Eksouzian |
| D726,364 S | 4/2015 | Weigensberg |
| D729,441 S | 5/2015 | Hua |
| 9,038,642 B2 | 5/2015 | Liu |
| D732,733 S | 6/2015 | Spagnolo et al. |
| 9,498,588 B2 | 11/2016 | Benassayag et al. |
| 2005/0017685 A1 | 1/2005 | Rees et al. |
| 2006/0093977 A1 | 5/2006 | Pellizzari et al. |
| 2008/0257367 A1 | 10/2008 | Paterno et al. |
| 2011/0220234 A1 | 9/2011 | Haas |
| 2012/0318882 A1 | 12/2012 | Abehasera |
| 2013/0042865 A1 | 2/2013 | Monsees et al. |
| 2013/0152922 A1 | 6/2013 | Benassayag et al. |
| 2013/0180533 A1 | 7/2013 | Kim et al. |
| 2013/0192617 A1 | 8/2013 | Thompson |
| 2013/0199528 A1 | 8/2013 | Goodman et al. |
| 2013/0213420 A1 | 8/2013 | Hon |
| 2013/0220315 A1 | 8/2013 | Conley et al. |
| 2013/0284190 A1 | 10/2013 | Scatterday et al. |
| 2013/0298905 A1 | 11/2013 | Levin et al. |
| 2014/0034070 A1 | 2/2014 | Schennum |
| 2014/0041655 A1 | 2/2014 | Barron et al. |
| 2014/0261499 A1 | 9/2014 | Hon |
| 2015/0020831 A1 | 1/2015 | Weigensberg et al. |
| 2015/0027467 A1 | 1/2015 | Liu |
| 2015/0027471 A1 | 1/2015 | Feldman et al. |
| 2015/0091501 A1 | 4/2015 | Claudepierre |
| 2015/0101625 A1* | 4/2015 | Newton ............... H05B 1/0244 131/329 |
| 2015/0118895 A1* | 4/2015 | Zheng .................... H01R 13/66 439/529 |
| 2015/0128976 A1 | 5/2015 | Verleur et al. |
| 2015/0157055 A1* | 6/2015 | Lord ..................... A24F 47/008 131/329 |
| 2015/0208728 A1* | 7/2015 | Lord ........................ A24F 7/00 131/329 |
| 2015/0305409 A1 | 10/2015 | Verleur et al. |
| 2016/0278436 A1 | 9/2016 | Verleur et al. |

(56) References Cited

U.S. PATENT DOCUMENTS

2016/0353804 A1* 12/2016 Lord .................. A24F 47/008
2017/0197046 A1    7/2017 Buchberger

FOREIGN PATENT DOCUMENTS

| CN | 201018927 Y | 2/2008 |
|---|---|---|
| CN | 203087525 U | 7/2013 |
| CN | 203182012 U | 9/2013 |
| EP | 0 358 114 A2 | 3/1990 |
| EP | 0 533 599 A1 | 3/1993 |
| EP | 0 845 220 A1 | 6/1998 |
| EP | 2 654 471 B1 | 10/2013 |
| KR | 101 011 453 B1 | 1/2011 |
| WO | 98/17131 A1 | 4/1998 |
| WO | 02/098390 A2 | 12/2002 |
| WO | 03/000324 A1 | 1/2003 |
| WO | 03/034847 A1 | 5/2003 |
| WO | 2007/078273 A1 | 7/2007 |
| WO | 2012/072762 A1 | 6/2012 |
| WO | 2013/034453 A1 | 3/2013 |
| WO | 2013/093695 A1 | 6/2013 |
| WO | 2013/116567 A1 | 8/2013 |
| WO | 2013/155645 A1 | 10/2013 |
| WO | 2013/159245 A1 | 10/2013 |
| WO | 2014/008646 A1 | 1/2014 |

OTHER PUBLICATIONS

European Patent Office Search Report dated Oct. 12, 2015 for EP Application No. 14159710.4, filed Mar. 14, 2014.
Andrus et al., "Nicotine microaerosol inhaler", Canadian Respiratory Journal, Nov./Dec. 1999, pp. 509-512, Vo. 6, No. 6.
"What is a MOSFET, what does it look like, and how does it work?" dated May 24, 2004, printed from the Internet Archive, i.e., the Wayback machine, which was archived on Mar. 5, 2010 ("TechPowerUp").
"What is a MOSFET, what does it look like, and how does it work?" dated May 24, 2004, printed from the Internet Archive, i.e., the Wayback machine, which was archived on Jul. 20, 2011 ("TechPowerUp").
Office Action issued in European Application No. 14159710.4, dated Apr. 24, 2017.
Non-Final Office Action dated Aug. 8, 2017 for U.S. Appl. No. 15/036,292, filed May 12, 2016, 10 pages.
International Search Report dated Feb. 10, 2015 for PCT/US14/065275, filed Nov. 12, 2014, 2 pages.
Written Opinion dated Feb. 10, 2015 for PCT/US14/065275, filed Nov. 12, 2014, 5 pages.
European Office Action dated Apr. 24, 2017 from European Application No. 14 159 710.4, 5 pages.

\* cited by examiner

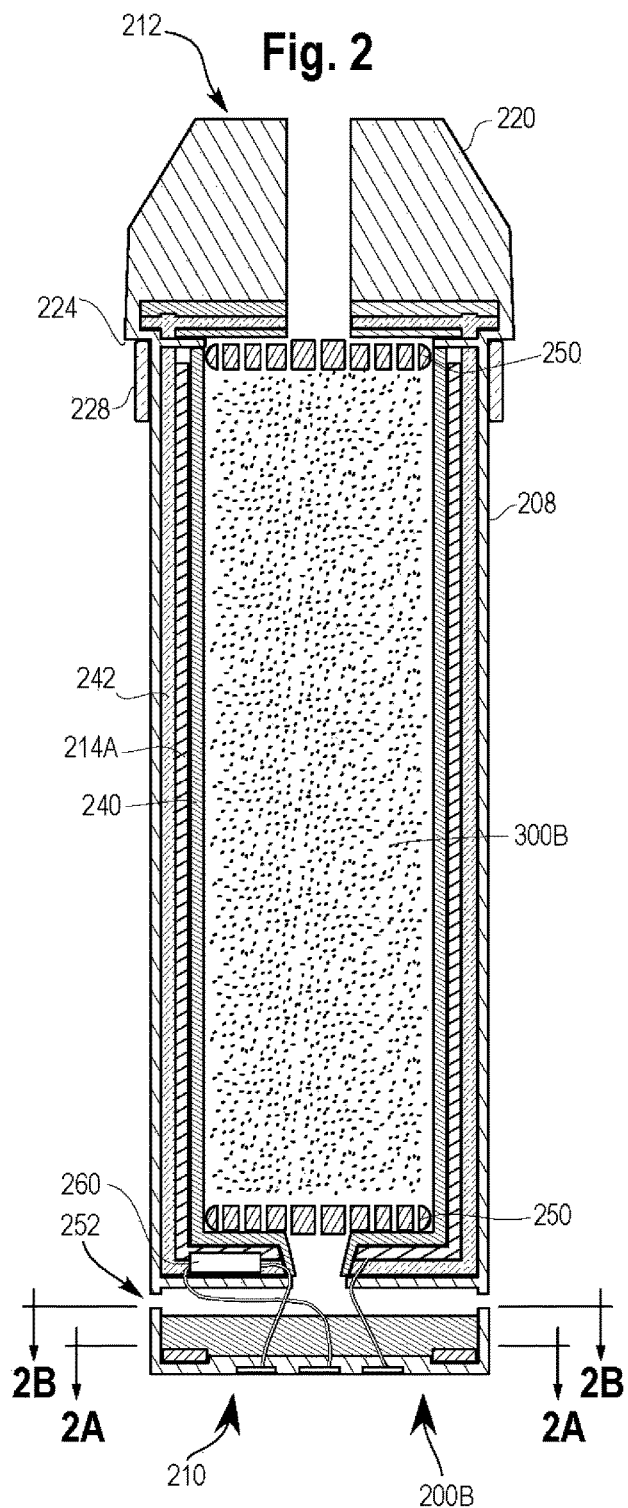
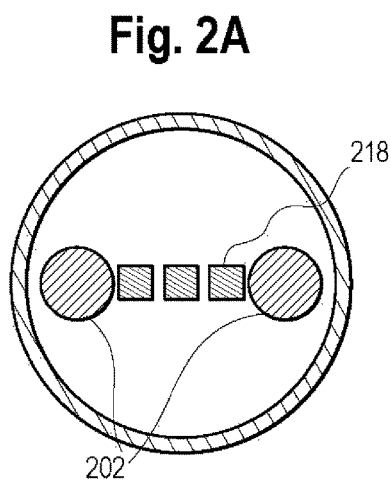
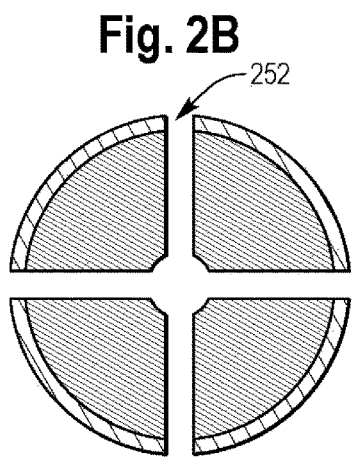

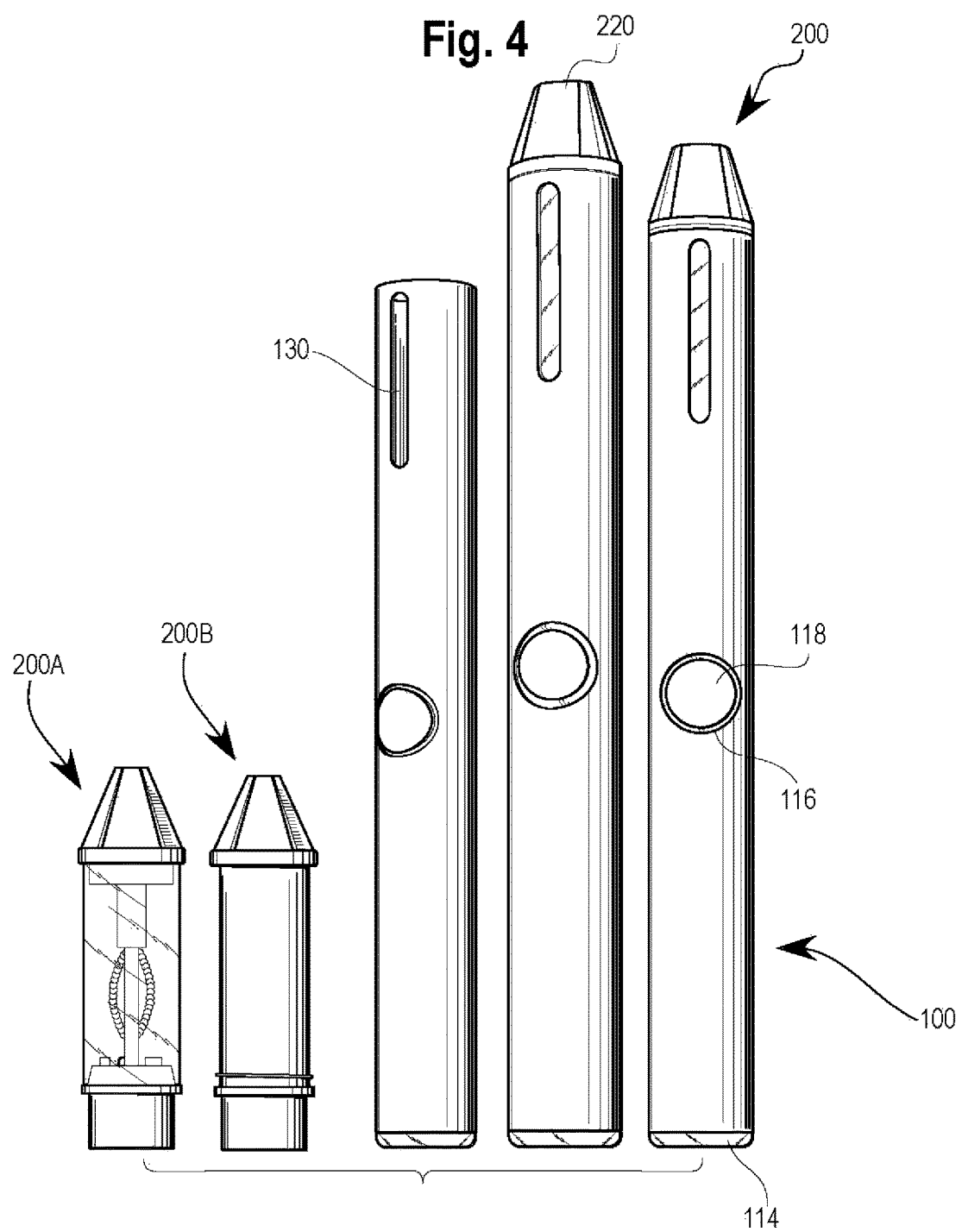

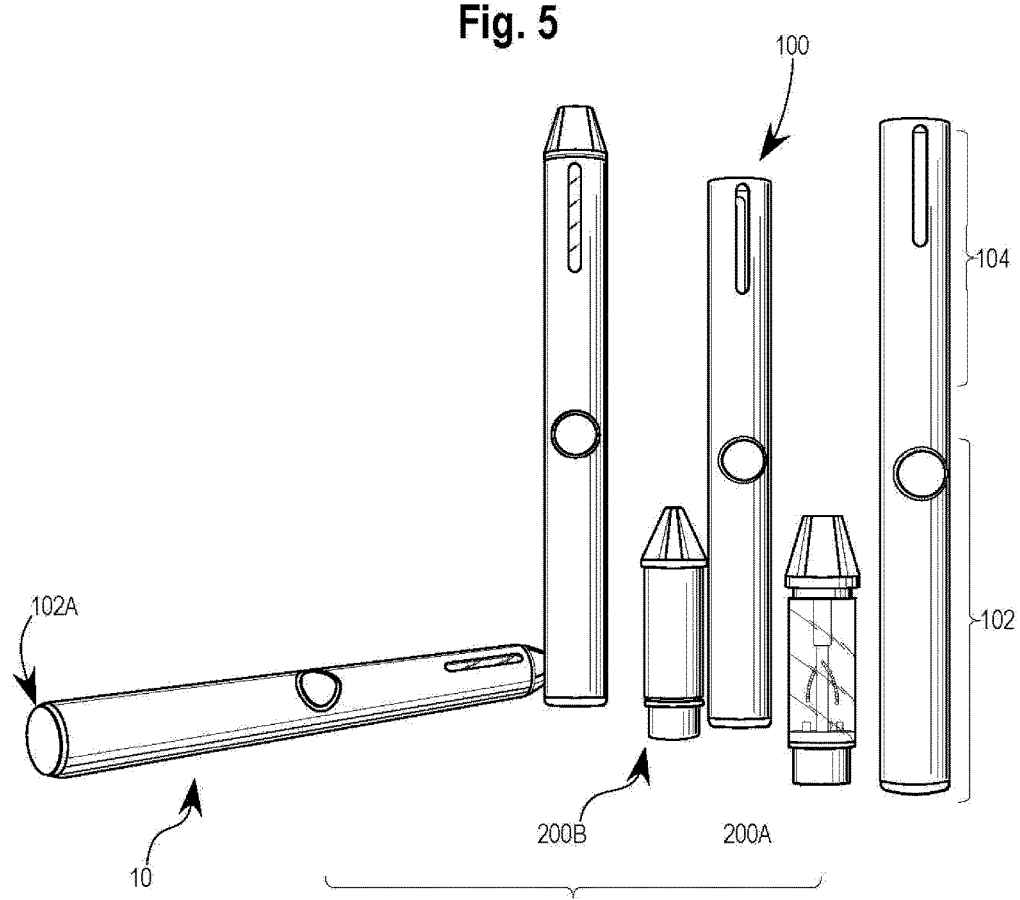

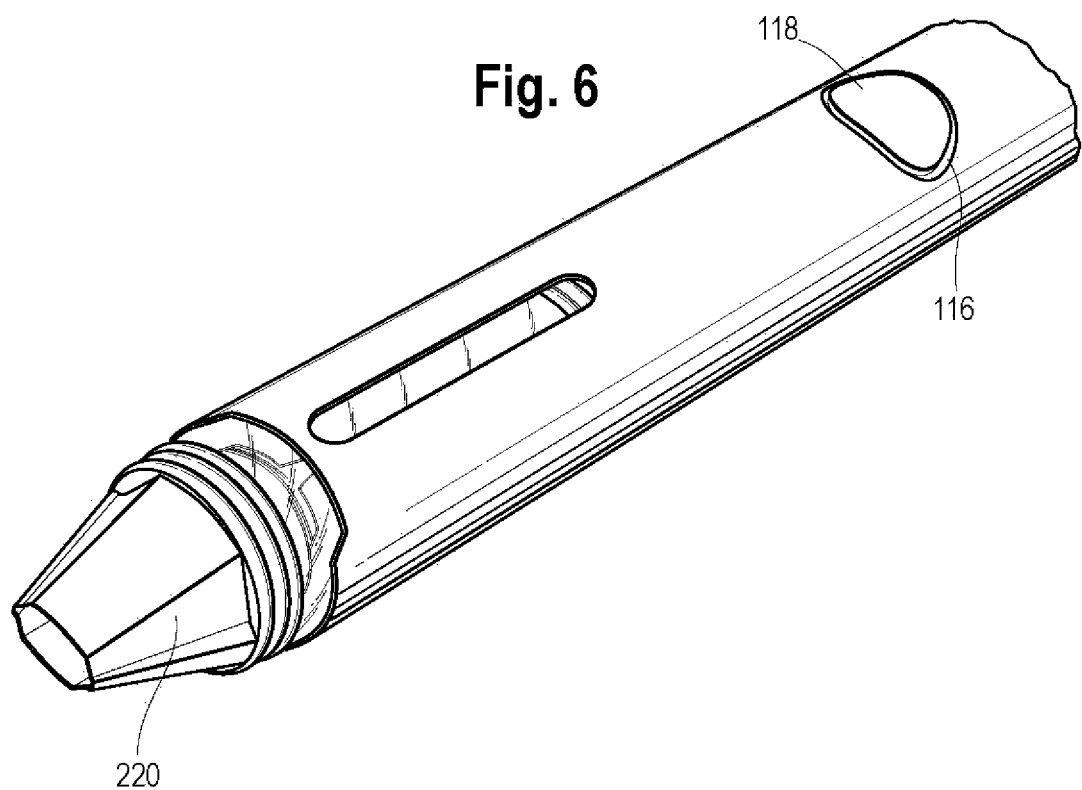
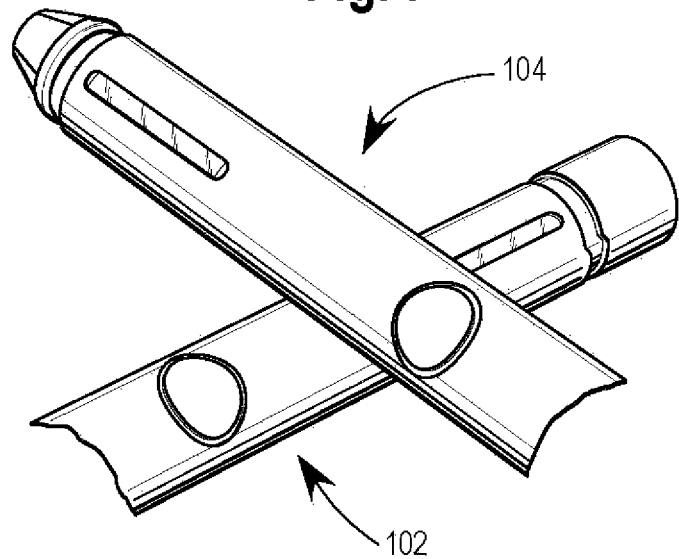

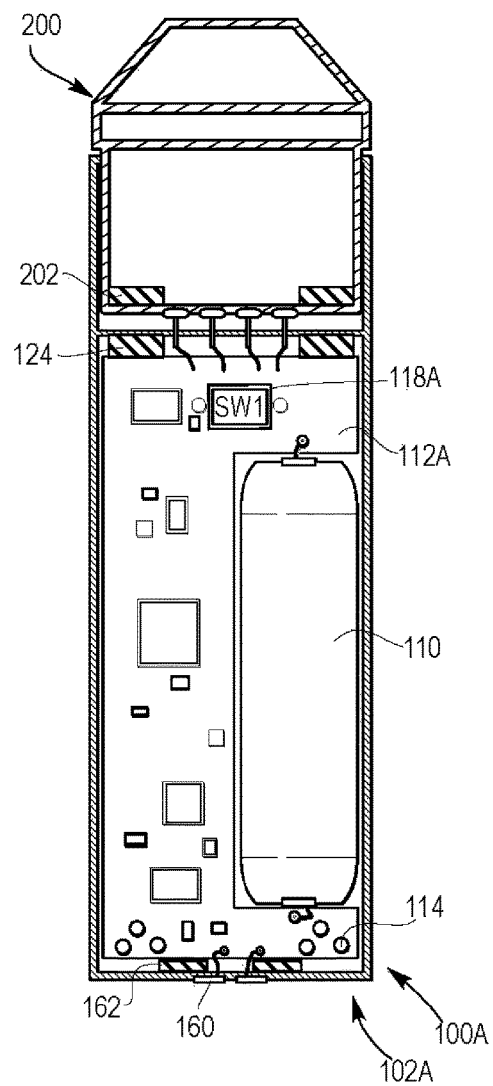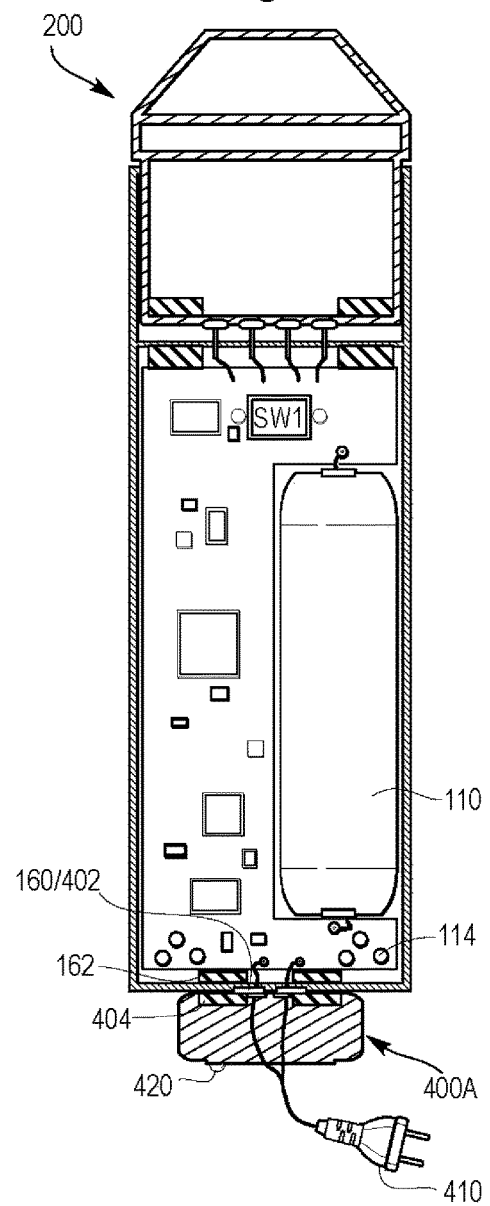

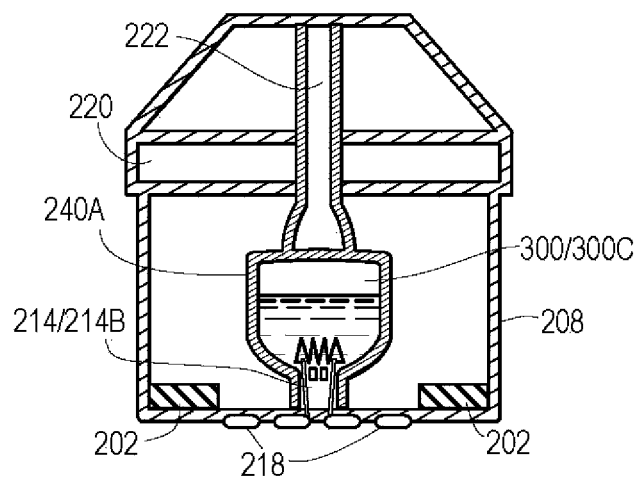
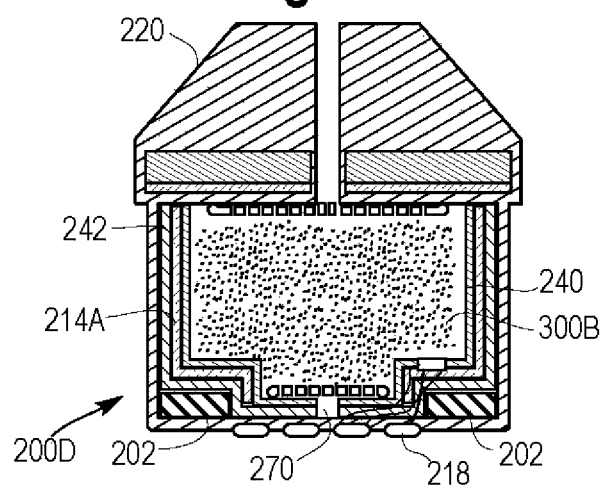

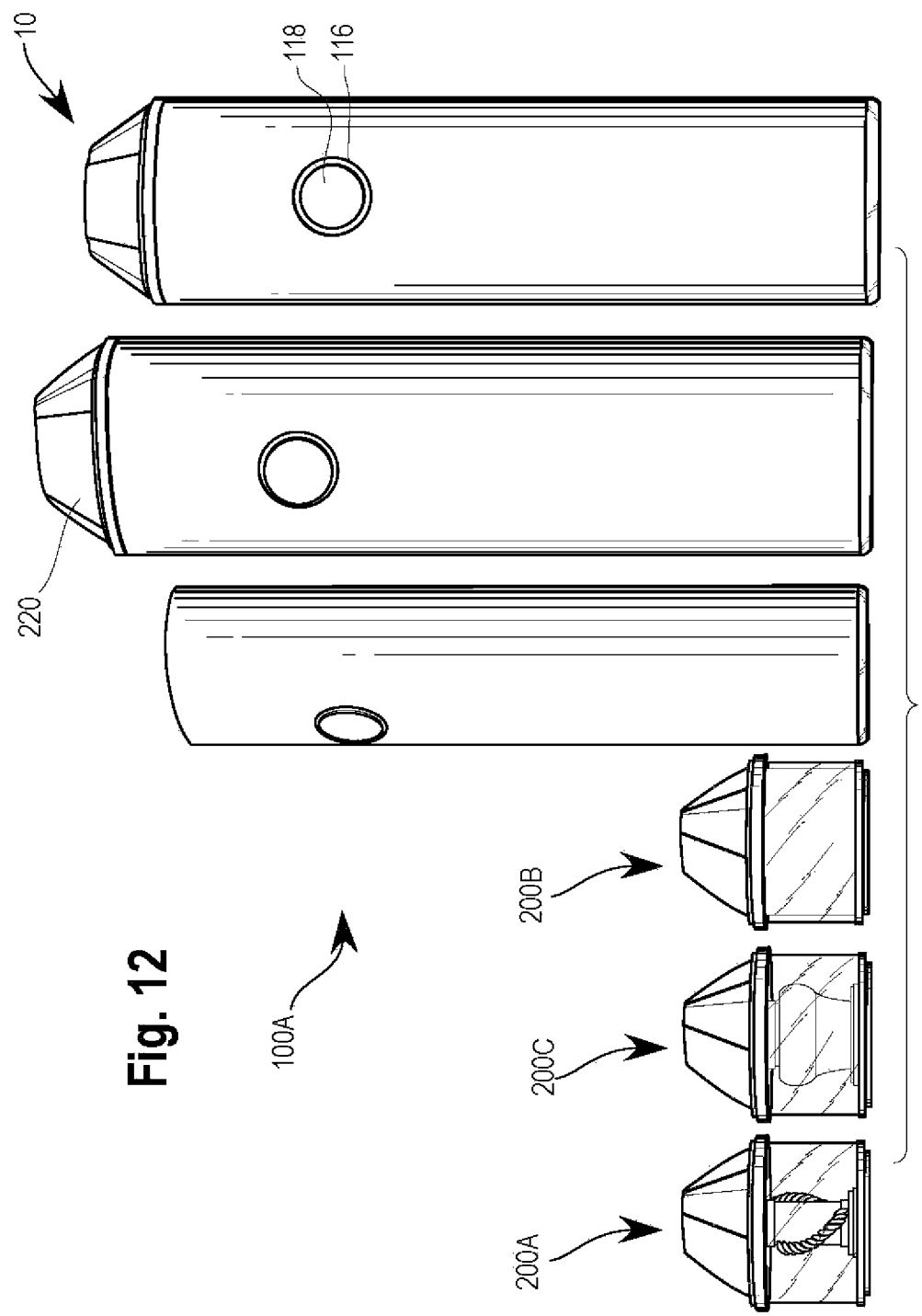

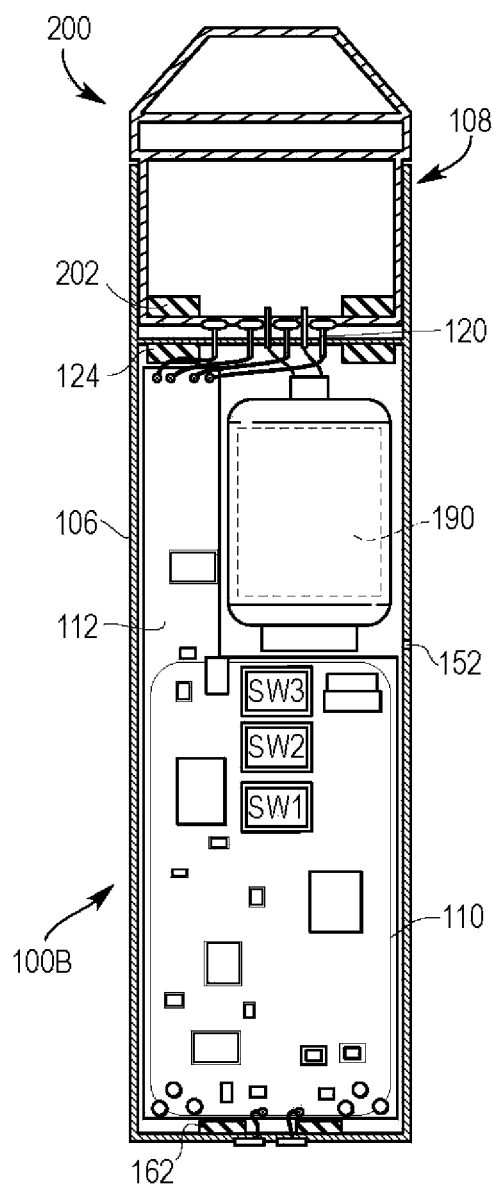
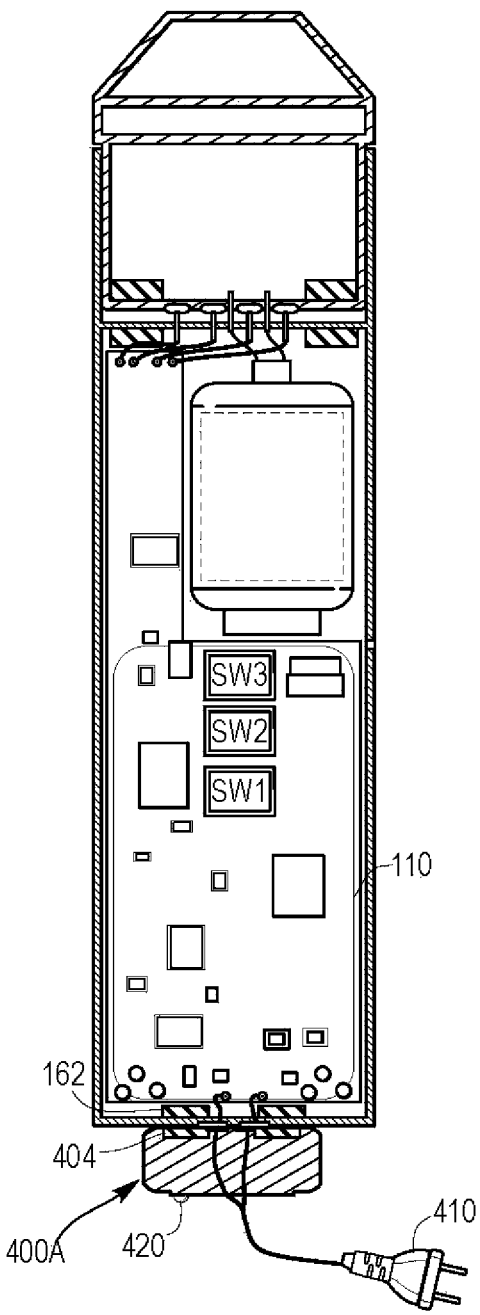

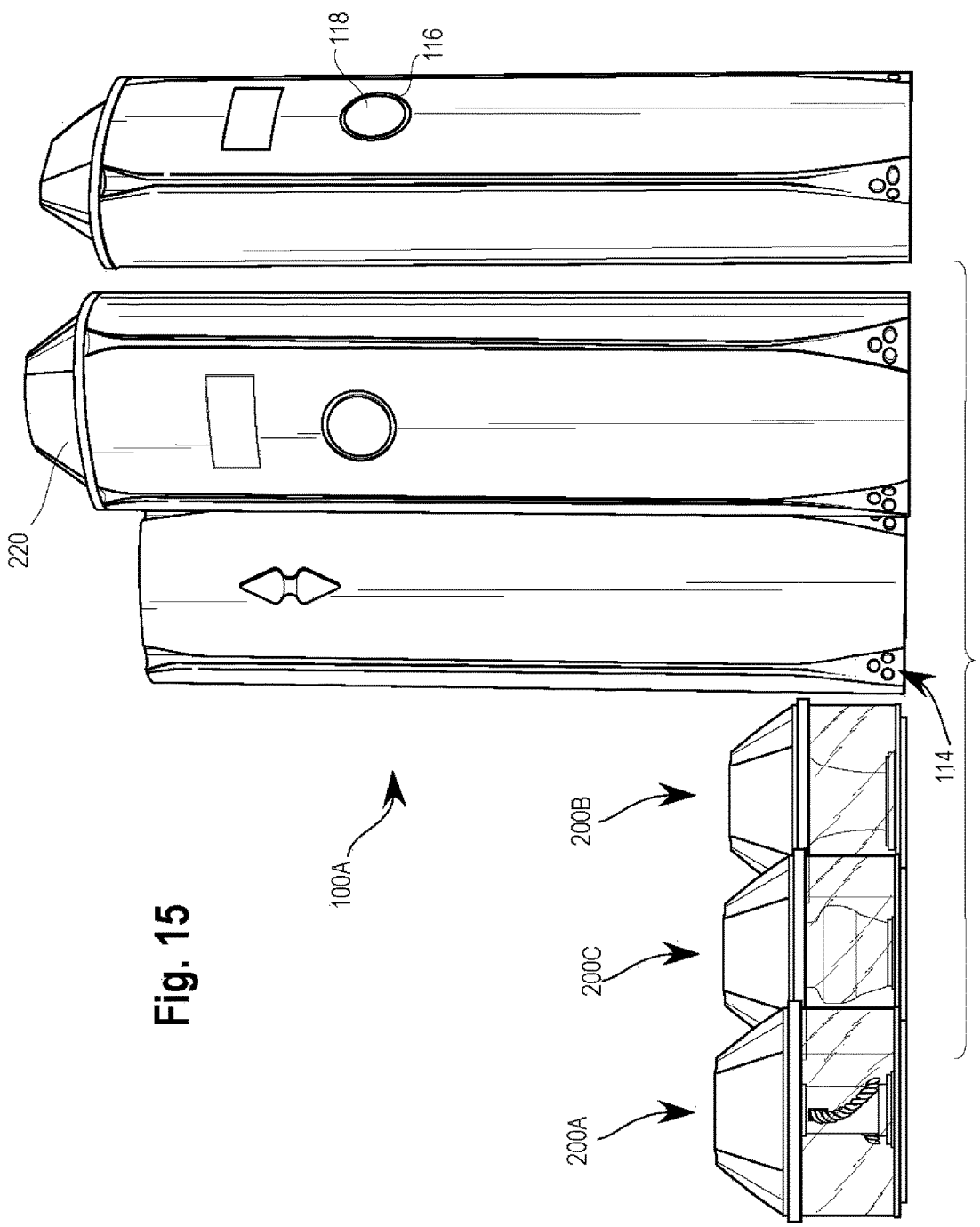

VAPORIZER

CROSS REFERENCE TO RELATED APPLICATIONS

This application claims the benefit of U.S. Provisional Application Nos. 61/903,344 filed Nov. 12, 2013, 61/937,851, filed Feb. 10, 2014, and U.S. Provisional Application No. 62/015,148, filed Jun. 20, 2014, the disclosures of which are hereby incorporated herein by reference in their entireties.

FIELD OF THE INVENTION

This invention relates to the field of vaporizers, which may also be referred to as electronic cigarettes.

BACKGROUND

Electronic cigarettes have recently emerged as a new product for providing nicotine through a smokeless inhalation process. Typically, implementations consist of a power supply (typically a battery) and an atomizing device. In reusable electronic cigarettes the two items are separated into a battery and a cartomizer, to allow the disposal and replacement of a nicotine containing fluid cartomizer while preserving the more costly battery and associated circuitry (microcontroller, switch, indicating LED, etc.) for additional use. In disposable electronic cigarettes, the two items are combined to integrate the functions into one unit that is discarded after either the battery energy or the nicotine containing liquid is exhausted.

The electronic cigarette liquid used to vaporize ingredients such as nicotine is generally a solution of propylene glycol (PG), vegetable glycerin (VG), or polyethylene glycol 400 (PEG400), as well as their mixtures to which a flavor and/or nicotine has been added. The solution is often sold in a bottle (for refilling by the user) or in disposable cartridges or cartomizers. Many different flavors are incorporated into these liquids, including those that resemble the taste of regular tobacco, menthol, vanilla, coffee, cola and/or various fruits. Various nicotine concentrations are also available, and nicotine-free solutions are also common.

BRIEF SUMMARY

Embodiments of a vaporizer, in accordance with the disclosure, may include a shell having a battery segment and a cartomizer receiving segment, the cartomizer receiving segment defining a chamber having an insertion end distal from the battery segment and a base end proximate to the battery segment; a cartomizer insertable into the chamber at the insertion end, the cartomizer including: an outer cartomizer shell, a holding structure provided within, and secured to, the outer cartomizer shell, the holding structure including a basin dimensioned to hold a vaporizable substance, a heating element provided within the basin operable to heat the vaporizable substance, cartomizer electrical contacts provided on the exterior of the cartomizer, cartomizer electrical circuitry operable to direct an electronic current between the cartomizer electrical contacts and the heating element, and a mouthpiece fluidly communicable with the basin, the mouthpiece extending from the insertion end of the chamber when the cartomizer is inserted in the chamber, wherein the heating element is activated by the current and is operable to heat the vaporizable substance to a vaporization temperature; a battery housed within the battery segment; battery electrical contacts provided between the base end of the chamber and the battery segment, the battery electrical contacts positioned to contact the cartomizer electrical contacts when the cartomizer is inserted in the chamber; battery electrical circuitry housed within the battery segment and operable to direct an electrical current between the battery, the battery electrical contacts, the cartomizer electrical contacts, the heating element, and the inserted cartomizer.

BRIEF DESCRIPTION OF THE FIGURES

FIG. 2 illustrates a front view of an embodiment of a cartomizer in accordance with the disclosure that may be inserted into the cartomizer chamber of the battery portion of FIG. 1, the outer shell of the first embodiment battery portion shown transparently so as to illustrate the inner components of the electronic cigarette.

FIG. 2A illustrates a lateral cross sectional view of the cartomizer of FIG. 2 illustrating the end of the cartomizer at the inserted end.

FIG. 2B illustrates a lateral cross sectional view of the cartomizer of FIG. 2 illustrating the air hole structure.

FIGS. 4-7 illustrate embodiments of electronic cigarettes comprising the first battery portion of FIGS. 1-3 and the cartomizers of FIGS. 1 and 2, in accordance with the disclosure.

FIG. 8 illustrates a front view of an embodiment of an electronic cigarette, in accordance with the disclosure, comprising another embodiment of a battery portion with the outer shell of the second embodiment battery portion shown transparently so as to illustrate the inner components of the electronic cigarette.

FIG. 9 illustrates a front view of the electronic cigarette of FIG. 8 with a charger attached, with the outer shell of another embodiment battery portion shown transparently so as to illustrate the inner components of the electronic cigarette.

FIG. 10 illustrates a front cross sectional view of an embodiment of a cartomizer in accordance with the disclosure.

FIG. 11 illustrates a front view of an embodiment of a cartomizer in accordance with the disclosure.

FIG. 12 illustrates embodiments of electronic cigarettes comprising the second battery portion of FIGS. 8-9 and the cartomizers of FIGS. 8-10.

FIG. 13 illustrates a front view of an embodiment of an electronic cigarette in accordance with the disclosure, with the outer shell of the embodiment of the battery portion shown transparently so as to illustrate the inner components of the electronic cigarette.

FIG. 14 illustrates a front view of the electronic cigarette of FIG. 13 with a charger attached.

FIG. 15 illustrates embodiments of the electronic cigarette of FIGS. 13-14 in accordance with the disclosure.

DETAILED DESCRIPTION

Figure 1:
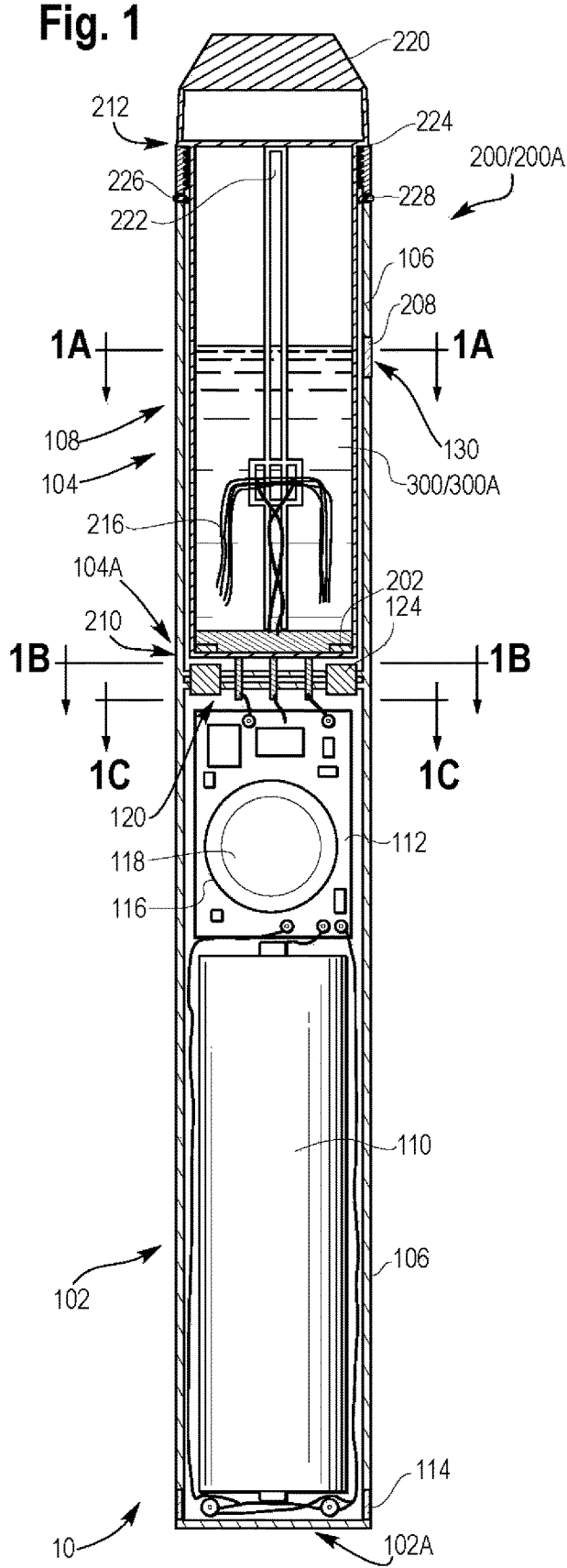
FIG. 1 illustrates a front view of an embodiment of an electronic cigarette of the disclosure comprising a first embodiment of a battery portion with an embodiment of a cartomizer for use with a vaporizable liquid inserted into a cartomizer chamber of the first embodiment battery portion, the outer shell of the first embodiment battery portion shown transparently so as to illustrate the inner components of the electronic cigarette.

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings are not to scale and in certain instances details have been omitted, which are not necessary for an understanding of the present invention, such as conventional details of fabrication and assembly.

Embodiments of a vaporizer, in accordance with the disclosure, may include a shell having a battery segment and a cartomizer receiving segment, the cartomizer receiving segment defining a chamber having an insertion end distal from the battery segment and a base end proximate to the battery segment; a cartomizer insertable into the chamber at the insertion end, the cartomizer including: an outer cartomizer shell, a holding structure provided within, and secured to, the outer cartomizer shell, the holding structure including a basin dimensioned to hold a vaporizable substance, a heating element provided within the basin operable to heat the vaporizable substance, cartomizer electrical contacts provided on the exterior of the cartomizer, cartomizer electrical circuitry operable to direct an electronic current between the cartomizer electrical contacts and the heating element, and a mouthpiece fluidly communicable with the basin, the mouthpiece extending from the insertion end of the chamber when the cartomizer is inserted in the chamber, wherein the heating element is activated by the current and is operable to heat the vaporizable substance to a vaporization temperature; a battery housed within the battery segment; battery electrical contacts provided between the base end of the chamber and the battery segment, the battery electrical contacts positioned to contact the cartomizer electrical contacts when the cartomizer is inserted in the chamber; battery electrical circuitry housed within the battery segment and operable to direct an electrical current between the battery, the battery electrical contacts, the cartomizer electrical contacts, the heating element, and the inserted cartomizer.

Further embodiments of a vaporizer may include a container having container walls provided proximate to the basin, the container dimensioned such that the vaporizable substance may pass from the container to the basin. The holding structure may further includes a stabilizing element connectable with the outer cartomizer shell, the basin secured to the stabilizing element. The stabilizing element may includes a first threaded portion threadably connectable with the outer cartomizer shell. The vaporizer may also include a container including container walls and a threaded container portion, the container dimensioned such that the vaporizable substance is passable from the between the container walls to the basin, and the stabilizing element includes a second threaded portion threadably engagable with the threaded container portion. The vaporizer may include at least one air passage provided through at least one hole in the outer shell and at least one hole in the container wall. The vaporizable substance may be a wax. The vaporizer may further include a cartomizer printed circuit board in electronic communication with the cartomizer electrical circuitry.

With reference now to FIGS. 1 and 2, an embodiment of an electronic cigarette 10 is provided in accordance with the disclosure. Electronic cigarette 10 may include a battery portion connectable with a vaporization unit or cartomizer 200 for holding a vaporizable substance 300. The battery portion may include a battery housing segment 102 provided proximate to the first end 102A of the battery portion, and a second cartomizer receiving segment 104 provided proximate a second end 104A of the battery portion. The battery portion may include an outer shell 106 for covering or protecting one or more of the components of battery portion 100 as may be internally provided as described herein. Outer shell 106 may be substantially constructed from metal, plastic, or any other known or to be developed material suitable for protecting internal components of electronic cigarette 10, including the electrical components described herein. Battery housing segment 102 and cartomizer receiving segment 104 may commonly share outer shell 106. A cartomizer chamber 108 may be provided within at least a portion of cartomizer receiving segment 104. A cartomizer 200 may be insertable into the cartomizer chamber 108 in accordance with embodiments of the disclosure. Shell 106 may cover cartomizer chamber 108 thereby protecting an inserted or received cartomizer 200.

Electrical components for operating electronic cigarette 10 may be provided within battery housing segment 102. A battery 110 may be provided in order to provide electrical power as may be required by various features of the electronic cigarette 10. In some embodiments, battery 110 may be disposable, such as an AA or AAA cell battery, while in other embodiments, battery 110 may be of a rechargeable type, for example a 13450 lithium ion battery, an 18650 2600 mAh lithium ion cell, or flat lithium ion 903180 cell rated at 2300 mAh. Multiple batteries 110 may be used in series to generate higher voltages capable of shortening times to achieve vaporization temperatures in the cartomizer 200. A printed circuit board (PCB) 112 may also be provided for controlling one or more functions of electronic cigarette 10. PCB 112 may be electrically connected to battery 110 through circuitry in order to direct current flow as required in accordance with the disclosure. PCB 112 may include one or more integrated circuit chips as well as a micro control unit. A boost chip may also be provided in order to amplify voltage with at least portion of circuitry, as may be required in order to accomplish various functions described herein. PCB 112 may include a light emitting diode (LED), a microcontroller, a plurality of capacitors, a plurality of transistors, and a plurality of resistors or any combination thereof. An accelerometer for sensing gravity shifts of electronic cigarette 10 may be further provided. The accelerometer may be operable to detect tilting or changes in orientation of battery portion 100, and PCB 112 may be accordingly operable to react to a shift in orientation detected by the accelerometer. For instance, electronic cigarette 10 including an accelerometer may be activated by shaking or inverting electronic cigarette 10. Any known or to be discovered circuitry or arrangement of the components of PCB 112 are contemplated within the disclosure in order to achieve the desired functions of electronic cigarette 10 as described herein.

A variety of indicator lights forming one or more illuminative indicators may be provided in embodiments of the disclosure. One such indicator may be a battery end indicator 114 provided as a ring extending about at least a portion of shell 106 at or proximate to first end 102A. In one such embodiment, battery end indicator 114 may be provided at or proximate to first end 102A and includes one or more LED lights having one or more colors. Each color may, for instance, indicate a status of electronic cigarette 10. The status may be associated with the power remaining of battery 110, an activation state of electronic cigarette 10, the heating level of an inserted cartomizer 200, or any other status which may be desirable to communicate to a user of electronic cigarette 10 through a light color. For instance, when electronic cigarette 10 is activated such that a user is either actively inhaling cigarette 10, as described in accordance with disclosure, or cigarette 10 is in a state such that the user could inhale, indicator 114 may be red or reddish. In such an embodiment, battery end indicator 114 could extend about at least a portion of the first end 102A such that when indicator 114 emanates a red or reddish color a user may associate the red color at or proximate to first end 102A with the red glow of a lit cigarette. In another embodiment, an indicator ring may be provided to illuminate one or more colors associated with the charge or power state of battery 110. For instance, battery end indicator 114 may illuminate green or blue when the battery is operating with a sufficient charge, and yellow or red when the battery is operating with a low charge such that the user should consider charging battery 110, in accordance with the disclosure. A ring indicator 116 may be provided on or proximate to an activation button 118, which may function to activate cigarette 10 as described herein in accordance with the disclosure. While activation button 118 may be provided on the surface of outer shell 106, and ring indicator 116 may substantially circumference button 118. Ring indicator 116 may include one or more LED lights having one or more colors to indicate various statuses of electronic cigarette 10. Status changes of electronic cigarette 10, such as insertion of cartomizer 200, activation of electronic cigarette 10 by pressing button 118, or deactivation of electronic cigarette 10 by pressing button 118 an additional time may each result in a different associated and predetermined color. The activation of the appropriate LED light or lights may be controlled by PCB 112. In embodiments where button 118 is coplanar or aligned with the surface of outer shell 106, as described herein, ring indicator 116 may also be coplanar or aligned with button 118 and the surface of outer shell 106. Another indicator light may be provided at or proximate to cartomizer end 104A. In one embodiment, in order to transmit a lighting effect from the battery segment 102, where battery 110 and PCB 112 may be housed, to the cartomizer end 104A, one or more LED lights may be provided in the cartomizer receiving segment 104 at or proximate to the battery segment 102. One or more clear tubes or optic fibers may be also be provided within or just below the surface of outer shell 106, with the tubes or fibers terminating at or proximate to the cartomizer end 104A. The resulting effect is an attractive, illuminative effect where the LED lights provided in the cartomizer segment are projected into and transmitted along the fibers. PCB 112 could potentially alternate or change the LED light colors projected into the fibers. The color alternation could be periodic, creating a steady change of colors, or the color alteration could be responsive to a status change of the electronic cigarette 10.

In order to provide an electrical connection between PCB 112 and an inserted cartomizer 200, an electrical connector 120 may be provided and may include a plurality of pogo pins 120. Pogo pins are devices used to establish connections between two circuits, and each may take the form of a cylinder containing one or more spring-loaded pins 122, each retractable upon compression, for instance by cartomizer 200 when it is inserted in cartomizer chamber 108. In one such embodiment, three pogo pins 122 may be provided, one for establishing positive current connection, one for establishing a negative current connection, and one for establishing a ground current connection. Each pogo pin 122 may be connected to PCB 112, which may control current outputted to pogo pins 122. For instance, PCB 112 may operate to vary or intermittently activate current flow to connector 120, the variation thereby regulating the activation of a heating element in a connected cartomizer. When cartomizer 200 is not received in cartomizer chamber 108, a head portion of each pogo pin may extend into cartomizer chamber 108. When cartomizer 200 is received in cartomizer chamber 108, the pins 122 are contacted and at least partially compressed into battery portion 102. Pins 122 may be contacted or pressed against electrical receivers provided on cartomizer 200 as described herein, thereby establishing an electrical connection between PCB 112 and cartomizer 200. Additional pins 122 are contemplated in embodiments of the disclosure, such as a fourth pin for providing an electrical connection to another element, such as the LED lights described above or a temperature sensor 260 described herein and illustrated in FIG. 2.

An additional embodiment of connector 120 may operate to identify information from an inserted cartomizer 200 based on voltage drop over one or more pins 122. For instance, connector 120 may include a controlling pin 122 from which connected PCB 112 may detect variations in voltage drop across the pin when connected to various types of cartomizers 200. Circuitry provided within a first type of cartomizer 200 may effectuate a first voltage drop over a controlling pin 122, while circuitry provided within a second type of cartomizer 200 may effectuate a second voltage drop over controlling pin 122 when cartomizer 200 is inserted in chamber 108. If PCB 112 detects a first voltage drop, the cartomizer 200 is identified as a first type of cartomizer, whereas if PCB 112 detects a second voltage drop, the cartomizer is identified as second type of cartomizer. A first cartomizer type may hold a first type of vaporizable substance 300, while a second cartomizer type may hold a second type of vaporizable substance 300. In one embodiment, connector 120 includes three pins 122: a positive pin, a ground pin, and a controlling pin. A controlling pin may also serve a dual function in that communication between a sensor 260 may also occur through a controlling pin 122. Other known or to be developed devices or connectors are contemplated within the disclosure for establishing an electrical current between PCB 112 and cartomizer 200.

Figure 1A:
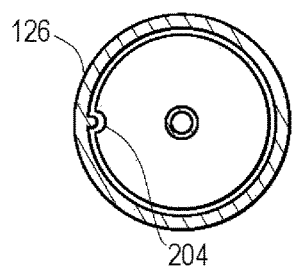
FIG. 1A illustrates a lateral cross sectional view of the electronic cigarette of FIG. 1 illustrating an electrical connector and magnets.
Figure 1B:
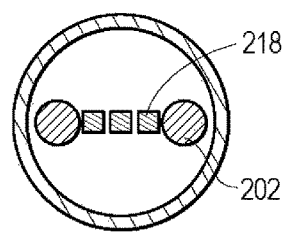
FIG. 1B illustrates a lateral cross sectional view of the electronic cigarette of FIG. 1 illustrating the end of the inserted cartomizer.

Various features may be further provided in embodiments of electronic cigarette 10 in order to secure and align cartomizer 200 within cartomizer chamber 108. For instance, at least one magnet 124 may be provided in or proximate to chamber 108. A magnet 202 of opposing polarity to magnet 124 may be placed on a surface of cartomizer 200 so as to secure cartomizer 200 within chamber 108 when magnets 124, 202 (see FIGS. 1A, 1B) contact each other. It should be understand and appreciated that, in some embodiments, battery portion magnet(s) 124 may attach to cartomizer metallic surface(s) 202 and, conversely, cartomizer magnet(s) 202 may attach to battery portion metallic surface(s) 124, thereby establishing a magnetic connection between battery portion 100 and cartomizer 200. Other known or to be discovered means of securing cartomizer 200 in cartomizer chamber 108 are contemplated within the disclosure, including but not limited to, snap fit connectors, friction fit, threaded insertion of cartomizer 200 into chamber 108, a suction fit using pressurized means or any other suitable method of securing known or to be developed in the art.

Figure 1C:
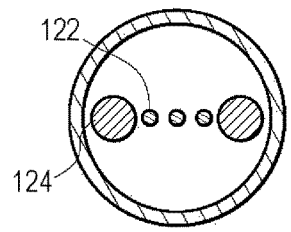
FIG. 1C illustrates a lateral cross sectional view of the electronic cigarette of FIG. 1 illustrating the cartomizer chamber.

One or more alignment features or mechanism may be included in order to ensure proper placement of cartomizer 200 in cartomizer chamber 108. In one embodiment, two magnets 124 may be provided proximate to connector 120 (see FIG. 1A), each magnet 124 having an opposed polarity. In this embodiment, two cartomizer magnets 202 (see FIG. 1B) may be provided of opposing polarity at an insertion end 210 of cartomizer 200. Because of the opposing polarities of magnets 124/202, the cartomizer 200 may only be inserted and secured in one direction or orientation, thereby facilitating alignment of cartomizer 200 within chamber 108. An alignment protrusion or peg 126 (see FIG. 1C) may be provided on a portion of an interior surface of chamber 108, and an alignment slit or slot 204 may be provided on a portion of cartomizer 200. Alignment protrusion 126 may be dimensioned to fit or slid along slit 204 so that cartomizer 200 may only be inserted in a particular, proper orientation. In another embodiment, a slit, crevice, or cutout may be provided on a portion of shell 106, with a matching protrusion provided on a portion cartomizer 200. For instance, a cutout may be provided on an upper rim of shell 106 at cartomizer receiving segment 104, while a matching protrusion may be provided on a portion of cartomizer 200 proximate to insertion end 210, with battery portion cutout engageable with the cartomizer protrusion when the cartomizer is properly aligned so as to ensure proper orientation of cartomizer 200 within chamber 108. Ensuring cartomizer 200 is properly oriented within chamber 108 in turn ensures proper contacting of cartomizer 200 with connector 120, and therefore proper functioning of electronic cigarette 10.

One or more windows 130 may be provided in outer shell 106 (see FIG. 1). Windows 130 may be made of a translucent material, such as glass or substantially clear plastic, in order to view internal components of battery portion 100. Window 130 may also be a slit cut into shell 106. For instance, in one embodiment, window 130 may be provided on or proximate to cartomizer receiving segment 104 and, more particularly, cartomizer chamber 108 so as to permit a user of electronic cigarette 10 to view the cartomizer 200 when it is inserted into cartomizer chamber 108.

One embodiment of cartomizer 200 for holding vaporizable material 300 is cartomizer 200A for holding a vaporizable fluid 300A, an embodiment of which is illustrated in FIG. 1. Vaporizable fluid 300A may be, for example, any known or to be developed fluid useful to vaporize, for inhalation nicotine, flavor or other desired ingredients in an electronic cigarette, such fluids include propylene glycol (PG), vegetable glycerin (VG), or polyethylene glycol 400 (PEG400), as well as their mixtures to which a flavor and/or nicotine has been added. Cartomizer 200A may be substantially elongate and insertable into chamber 108. Chamber 108 is defined by outer shell 106 and electrical connector 120. An insertion end 210 of cartomizer 200A, defined opposite of a mouthpiece end 212, may be inserted into the chamber first and may ultimately contact or be positioned proximate to connector 120 of battery portion 100. Cartomizer 200A may include a body 208 for holding fluid 300A. At least a portion of body 208 may be composed of translucent or substantially translucent material, such as glass or plastic, so that a user may see fluid 300A held within. The portion of body 208 composed of translucent material may be alignable with window 130 and may be proximate to LED lights or fiber optics so as to illuminate cartomizer 200A as it is inserted into chamber 108. The illumination may occur automatically upon insertion, or may be programmed to illuminate upon activation or manipulation of a switch, such as button 118.

In order to vaporize fluid 300A, a heating element 214 and a wicking element 216 may be provided within cartomizer body 208. An electrical current may be transmitted to heating element 214 through circuitry in electrical communication with electrical contacts, which contact pins 122 (see FIG. 1A) when cartomizer 200A is inserted into chamber 108. Once fluid 300A is heated to an optimal vaporizing temperature, the user may inhale the vaporized fluid 300A through a mouthpiece 220 provided on body 208 at or proximate to mouthpiece end 212. The vaporized fluid may travel through an inhalation tube 222 in fluid connection with heating element 214 and wick 216. Inhalation tube 222 may also be in fluid communication with one or more holes or ducts provided, for instance, in sides of outer shell 106 in order to permit air flow through cartomizer body 208. The electrical current transmitted to heating element 214 may be controlled by PCB 112 through connector 120 when cartomizer 200A is inserted into chamber 108. The electronic cigarette 10 may be manually controlled, as a user may press button 118 to initiate a charge to heating element 214, which in turn may heat fluid 300A to a vaporized temperature which a user may inhale through mouthpiece 220. An automatically heating version of electronic cigarette 10 is also contemplated with disclosure, where a pressure switch integrated with connector 120 may activate current flow from PCB to heating element 214 rather than by manual activation from switch 118.

So that a user may refill fluid 300A held in body 208, mouthpiece 220 may be removable from body 208. Mouthpiece 220 may include a screw thread 224 so that mouthpiece 220 may be threadably engaged with mouthpiece end 212 of body 208 or, alternatively, may be press fit onto or into mouthpiece end 212 of body 208. A bushing 226, which may be a ring formed from plastic, rubber, or any other suitable material, may be provided to help stabilize and retain cartomizer 200 tightly fit in chamber 108. Additionally, a colored ring or logo 228 may be provided about a portion of cartomizer body 208 in order to identify the type or cartomizer being used.

With reference now to FIGS. 2, 2A and 2B, an additional embodiment of cartomizer 200B is provided for holding a dry vaporizable material 300B, such as dry tobacco. A container 240 may be provided within cartomizer body 208. Container 240 may be made from a material having a high thermal conductivity, such as metal, in order to transmit heat from a heating element 214A provided about at least a portion of container 240. In that at least a portion of heating element 214A may be provided about at least a portion of container 240, the material 300B provided within container 240 may be heated from multiple sides, similar to an oven, as opposed to from a single concentrated heat source. As an electrical current is transmitted to heating element 214A, the interior of container 240 may be heated to a desired vaporizing temperature. Heating element 214A may be substantially comprised of a non-conductive material, such as a polyimide flex harness material, with a conductive material, such a copper or other metal wiring shaped into a wire or flat ribbon, dispersed throughout the non-conductive material. The conductive material may be intertwined or wound throughout the non-conductive material in order to increase the heated surface area as well as to increase the impedance of the conductive material, which may then be electrically connected to PCB 112 through connector 120 when cartomizer 200B (See FIG. 2) is inserted in cartomizer chamber 108 (See FIG. 1). The impedance value of the conductive material may be 2-3 ohms in some embodiments, and in other embodiments a maximum of 1 ohm. In some embodiments, heating element 214A may be provided around the majority of cartomizer body 208, and in some embodiments heating element 214A may be provided proximate to only a portion of cartomizer body 208. For instance, heating element 214A may be provided only proximate to insertion end 210, in order to provide a greater portion of heating through convection rather than through conduction. In some embodiment, heating element 214A may be provided about all or the majority of body 208, and PCB 112 may be operable in order to vary the amount of heating provided through convection rather than conduction. For instance, only the portion of heating element 214A proximate to insertion end 210 may be activated in order to heat vaporizable substance 300B through convection, or all or nearly all portions of heating element 214A may be activated in order to increase the conduction heating of substance 300B. PCB 112 may operate to switch between a conduction heating and a convection heating.

An insulating material 242 may be further provided within body 208 in order to control or regulate the heat distribution. Insulating material 242 may be provided around at least a portion of the exterior of heating element 214A in order to insulate body 208 from excess heat temperature, which may transmit to outer shell 106 (See FIG. 1). Insulating material 242 may also be provided between heating element 214A and container 240 so as to regulate or control heat transmitted to container 240.

One or more screens 250 may be provided within body 208 in order to contain dry material 300B within container 240, as well as to filter circulated air. Air may be circulated by providing one or more holes 252 in the cartomizer body 208. In one embodiment, holes 252 form a "t" shape (See FIG. 2B) from which the center of the "t" is substantially aligned with a hole leading to container 240. Holes 252 may be capable of alignment with one or more holes on the outer shell 106 of battery portion 100 so that air from the environment may pass through holes 252 and into container 240 where material 300B is provided. Holes 252 may be provided proximate to the inserted end 210. Screens 250 may be provided either at or proximate to inserted end 210, mouthpiece end 212, or both. In some embodiments, container 240 is removable from the rest of cartomizer body 208. Mouthpiece 220 may be removable or detachable, for instance through a screw thread, so as to permit access to container 240. An upper screen 250 may be attached or manufactured integrally with mouthpiece 220 so as to be removed with mouthpiece 220.

A sensor 260 may be included in some embodiments of cartomizer 200. Sensor 260 may operate to sense vaporizing temperature, and may be electronically communicative with PCB 112 so as to provide sensory information to PCB 112, which may be consequently transmitted to one of the LED indicators provided in electronic cigarette 10 as described in accordance with the disclosure. For instance, indicator 118 (See FIG. 1) may illuminate a certain color when sensor 260 has detected that vaporization temperature in container 240 has been reached and the user may proceed to inhale vaporized material 300. PCB 112 may also including safety protocols for automatic shutoff in the event that sensor 260 records a temperature above a preset vaporization temperature range, which may indicate material 300 (including, for example, 300A, 300B, 300C) is actively burning or about to burn. Thus, sensor 260 may operate as a thermistor. A vaporization range for many materials 300 may be between about 190 degrees Celsius and about 240 degrees Celsius, and in some embodiments the vaporization temperature may be at about 230 degrees Celsius. In this vaporization temperature range, active ingredients of the vaporization material 300 may begin to vaporize without actively burning, which may occur at about 400 degrees Celsius or higher for some materials. PCB 112 may operate to control the vaporization temperature, for instance regulating a maximum vaporization temperature or controlling the vaporization actual temperature. In one embodiment, PCB 112 may control or regulate vaporization temperature within 10 degree Celsius, and in another embodiment PCB 112 may more finely control or regulate vaporization temperature within 1 degree Celsius, based on a selected or desired vaporization temperature as inputted by a user of electronic cigarette 10. It should be understood and appreciated that communication between sensor 260 and PCB 112 may be bidirectional so that sensor 260 may operate to control at least portions of vaporizer functions or to transmit information to PCB 112 and additionally receive information from PCB 112, which operates to control electronic cigarette 10.

Figure 2C:
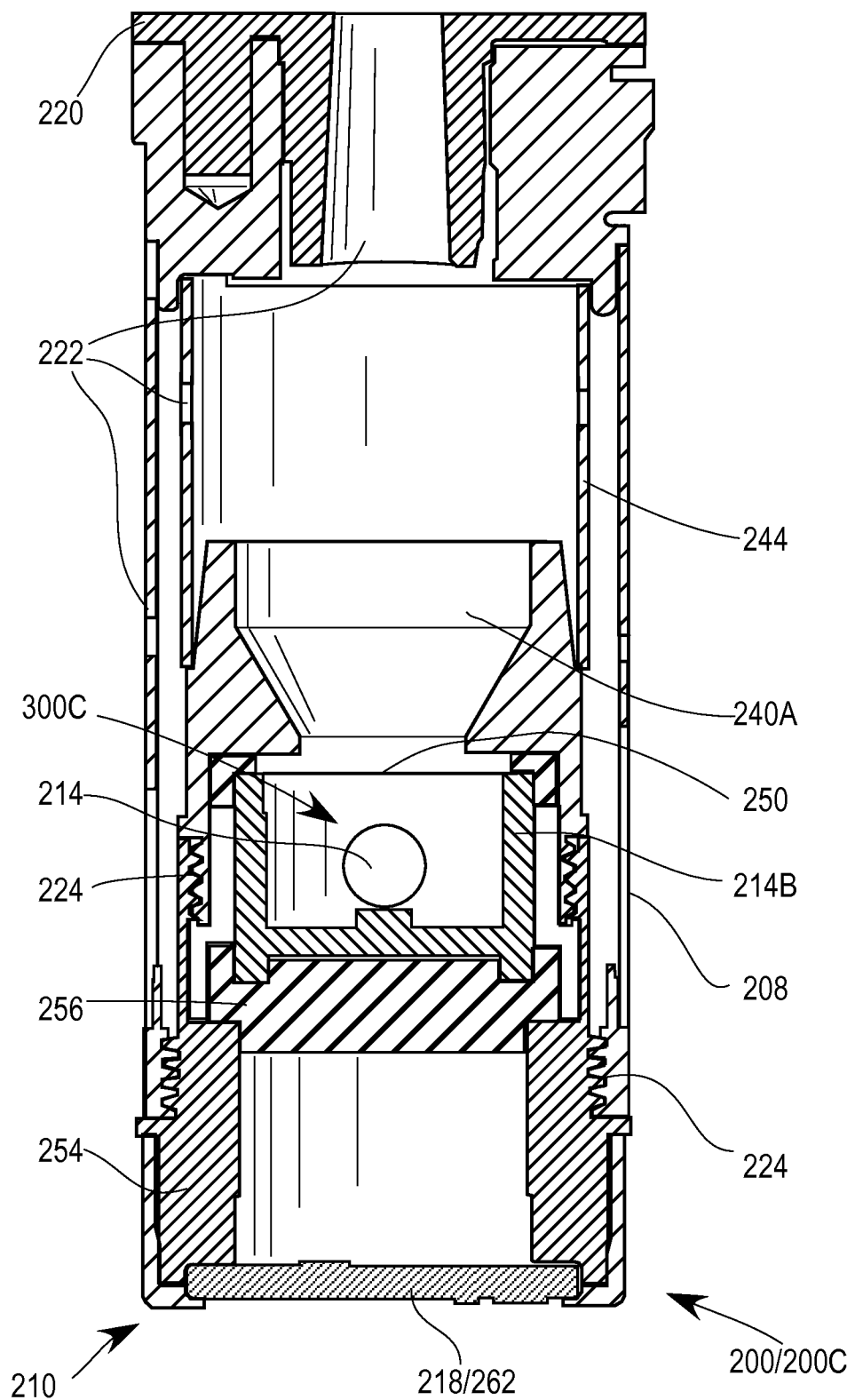
FIG. 2C illustrates a front view of an embodiment of a cartomizer in accordance with the disclosure that may be inserted into the cartomizer chamber of an embodiment of a battery portion of the disclosure, the outer shell of the first embodiment battery portion shown transparently so as to illustrate the inner components of the electronic cigarette.

FIG. 2C illustrates an additional embodiment of cartomizer 200C which may be inserted into cartomizer chamber 108 (FIG. 1) and utilized for vaporization of a vaporizable wax 300C. Cartomizer 200C may include an outer cartomizer shell or body 208 for housing and protecting internal components of cartomizer 200C. Outer shell 208 may include a threadable end 224 provide proximate to insertion end 210, and distal to mouthpiece 220. In one embodiment, mouthpiece 220 may be connected to outer shell 208 while in another embodiment mouthpiece 220 may be removable from outer shell 208, for instance from threading or a friction held push fit. Through threading 224 proximate to insertion end 210, outer shell 208 may be threadably engagable with a holding structure 254, which may be provided for securing a heating element 214 provided within a bowel or basin 214B. As part of holding structure 254, a stabilizing element may be provided 256. In one embodiment, basin 214B is secured to stabilizing element 256. Stabilizing element 256 may be constructed for silicone rubber or any other known or to be discovered material which may be provided to secure basin 214B while embodying the necessary thermal properties for contacting basin 214B. In one embodiment, basin 214B is composed of ceramic. Proximate to basin 214B may be a wax container 240A, and a screen or mesh 250 may be provided between basin 214B and container 240A. Container 240A may include a threaded portion 224 for removable engaging with holding structure 254. In this regard, holding structure 254 may feature two threadings 224—a first threading for engagement with outer shell 208 and a second threading for engagement with container 240A. A container cover 244 may be further provided and may include cover walls which substantially surround the upper and open portion of container 240 opposite heating element 214 and basin 214B. In one embodiment, cover 244 is secured to a portion of mouthpiece 220 such that when outer cover 208 is removed along with mouthpiece 220, cover 244 is further removed thereby exposing container 240A so that it may be refilled with additional wax 300C. Airflow passage 222 may be provided as a first passage within the wall of container cover 244, a second passage within the wall of outer shell 208, and an tube leading through mouthpiece 220. Multiple first passages and multiple second passages may be provided as described. In order to discourage back flow of vapor, the one or more first passages may be placed closer to mouthpiece 220 than the one or more second passages. In this arrangement, vaporized wax 300C may travel from heating element 214 through container 240A and the first passage within the wall of cover 244, through a circumferentially outer passage between cover 244 and outer shell 208, and out through mouthpiece 220 as a user inhales. Electrical wiring may be provided from heating element 214 to a cartomizer PCB 262, which may operate to control the functioning of the cartomizer including activation of heater 214. In association with PCB 262 may be electrical contacts 218 for permitting electrical communication with battery portion 100.

Figure 3:
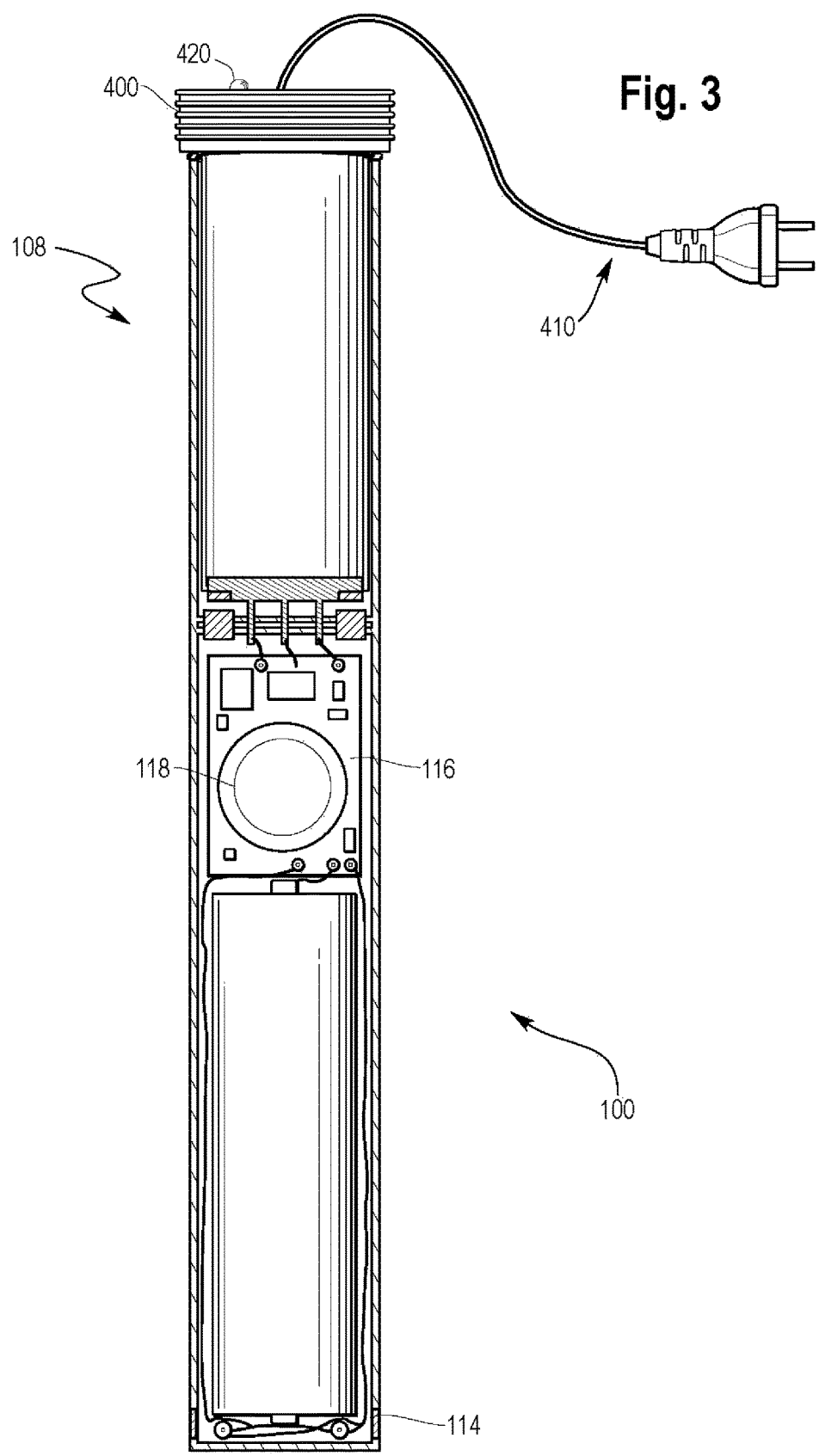
FIG. 3 illustrates a front view of an embodiment of the battery portion of FIG. 1 with an embodiment of a charger, in accordance with the disclosure, inserted into the cartomizer chamber, with the outer shell of the first embodiment battery portion shown transparently so as to illustrate the inner components of the electronic cigarette.

As shown in FIG. 3, a charger 400 may be inserted into chamber 108 (FIG. 1) in order to charge battery 110 (FIG. 1) in embodiments where battery 110 may be rechargeable. Through its insertion into chamber 108 and contact with connector 120, charger 400 may provide an electrical charge to battery 110. Charger 400 may include a plug 410 for connecting charger 400 to a power source, which in one embodiment is a wall socket. Other plugs 410 for different power sources are contemplated within the disclosure, including USB connections and other known or to be developed power sources. An indicator light 420, which may be an LED light, may be provided on charger 400 in order to indicate a charging status, for instance when charger 400 is connected with a power source. PCB 112 may operate to change other indicators, for instance LED indicators 114/116, to indicate the charging status of electronic cigarette 10. In accordance with the disclosure, and illustrated for instance in FIG. 9, charger 400 may be connectable to battery portion at or proximate to first end 102A. Furthermore, as also illustrated for instance in FIG. 9, charger magnets 404 are contemplated within the disclosure in order to securely couple charger 400 to battery portion 100. In one embodiment, a metallic surface 404 is provided and positioned so as to be adjacent to magnets 124 or magnets 162 (depending on the embodiment of the disclosure). In another embodiment, a metallic surface 124 or 162 in order to magnetically couple battery portion 100 with charger magnets 404. Additionally, charger magnets 404 may be provided having opposing polarities as battery portion magnets 124 or 162.

With regards to PCB 112, as previously discussed for instance in reference to FIG. 1, and related electrical components, functioning, and control of vaporizer 100, a variety of controls or commands are contemplated in associated with the operation of vaporizer 100. Various LED indicators 114, 116 may be utilized in conjunction with PCB 110 in showing operation states or statuses of vaporizer 100. For instance, the pressing of button 118 a preset number of times, which may be 3 times, within a preset time period, which may be 2 seconds, may result in locking or unlocking the vaporizer. Ring indicator 116 may then change illuminated colors to indicate a lock state of vaporizer 100. In a lock state, vaporizer may not function to activate a heating element 214/214A/214B of an inserted cartomizer 200. A low battery voltage may also be indicated to a user by illuminating and possibly flashing a predetermined color through indicator 116. In one embodiment, a low battery state is indicated when the battery voltage of battery 110 falls below about 3.2V. Activation of heating element 214/214A/214B may be accomplished by pressing or holding button 118. A cutoff feature may programmed into either PCB 112 or cartomizer PCB 262 such that heating element 118 will be disabled if button 118 is actuated for longer than a preset time, which may be 10 seconds in one embodiment and 30 seconds in another embodiment. While button 118 is actuated, and accordingly heating element 214 of an inserted cartomizer 200 is activated, indicator 116 may illuminate a predetermined color. Additionally, PCB 112 may operate to detect the type of inserted cartomizer 200, namely what type of vaporizable substance 300 the inserted cartomizer 200 is designed to hold and vaporize, and accordingly ring indicator 116 may illuminate a preset color associated with the inserted cartomizer 200 type. For instance, ring indicator may illuminate in a white, red, and green color when a first, second, and third cartomizer type is inserted, respectively. For some vaporizable substances 300, particularly many varieties of dry tobacco 300B, heating element may need to heat the substance for a certain time period before the substance is vaporized and may be inhaled by the user. In this situation, button 118 may be held for a certain time, which may be 3 seconds, before ring indicator illuminates indicating the user may inhale the vaporized substance. Furthermore, in the event an error in the PCB 112 programming occurs, a reset feature may be incorporated. For instance, pressing and holding button 118 for a certain time period, which may be three (3) seconds, while no cartomizer is inserted may operate to reset the programming to a default programming.

FIGS. 4-7 further illustrate the embodiments of electronic cigarette 10 provided in FIGS. 1-3, in accordance with the disclosure.

FIGS. 8 and 9 illustrate an additional embodiment of an electronic cigarette 10 having a battery portion 100A for receiving a cartomizer such as cartomizer 200 or cartomizer 200B. PCB 112 may operate to perform a variety of functions including, such vaporization temperature control or regulation, voltage boost, accelerometer, or various drivers for controlling LED functioning. One or more LED indicators 114 may be provided and, in one embodiment, a set of three LED lights of variable colors are provided proximate to battery end 102A of the battery portion 100A. Magnets 124/202 may be provided in order to retain cartomizer 200 within cartomizer chamber 108. A switch 118A may be provided in order to manually activate or otherwise control electronic cigarette 10.

A battery charger 400A, having charging contacts 402, may be attached or connected to charging contacts 160 provided on outer shell 106, or otherwise exposable to the environment. In one embodiment, charging contacts 160 are positioned at or proximate to battery end 102A. Charging contacts 160, 402 may include a first positive contact and a second negative contact. In order to secure charging contacts 160 against corresponding charging contacts 402 of charger 400A, one or more magnets 162 may be provided proximate to charging contacts 160. Magnets 162 may then be capable of engaging with charger magnets 404 provided on portion of charger 400A such that magnets 162, 404 are adjacent to each other when contacts 160, 402 are contacting one another. In order to ensure the proper alignment of contacts 160, 402, two magnets 162 may be provided with opposed polarities, and two charger magnets 404 may be provided with opposed polarities. These opposed polarities may ensure proper orientation of charger 400A when it is connected to battery portion 100A. In some embodiments, battery portion magnet(s) 162 may operate to magnetically attract and connect a metallic charger surface 404, or charger magnets 404 may operate to magnetically attract and connect a metallic battery surface 162, each of these embodiments thereby operating to magnetically couple charger 400 with battery portion 100. An indicator light 420, which may be an LED, may be provided to indicate a charging status of battery 110. A charging extension 410 may be provided so as to connect charger 400A to a power source or, alternatively, a power source may be internally provided within charger 400A. Charging extension 410 may be an AC wall adapter to USB and USB cord to magnetic plug. Any charger 400 of the disclosure may contain OverVoltage and OverCurrent protection in order to prevent over charging of battery 110 thereby assuring long battery life and in order to reduce the likelihood of battery 110 overheating. In one embodiment, charger 400 is rated at approximately 1000 mA current, which for some embodiments will equate to approximately two hours of battery life. The battery life will vary depending on battery selection and number of batteries 110 used in a given embodiment.

Referring now to FIG. 10, an embodiment for a cartomizer 200C is provided for holding a vaporizable substance 300. Cartomizer 200C may be used as an alternative cartomizer to 200/200B cartomizers, for example. Vaporizable substance 300 in cartomizer 200C may be a wax, oil or gel 300C. In cartomizer 200C, heating element 214 may be provided at the base of a basin 214B, which may or may not be removable from cartomizer body 208. Basin 214B may be dimensioned to hold wax, oil or gel 300C while heating element 214 may elevate the temperature within basin 214B to a vaporization temperature range, as controlled by PCB 112. Once the wax, oil or gel 300C is vaporized, a user may inhale the vapor through an inhalation tube 222 and out through mouthpiece 220. In some embodiments, mouthpiece 220 is removable through a friction fit, threaded connection, or any other known or to be developed connection means.

One or more O-ring seals may also be provided proximate to the mouthpiece to ensure a fluid tight connection between mouthpiece 220 and cartomizer body 208.

FIG. 11 shows an additional embodiment of a cartomizer 200D for holding a dry vaporizable substance 300B. Cartomizer 200D may be used as an alternative cartomizer to 200/200B cartomizers, for example. Dry substance 300B may be held in a removable liner or container 240. Cartomizer 200D may also include heating element 214A and insulation material 242, each of which may be similarly provided and oriented as previously described with respect to cartomizer 200B. An air flow hole or aperture 270 may be provided at the base of cartomizer 200D. This airflow hole 270 may be provided off plane or misaligned with respect to electrical contacts 218. Airflow hole 270 may align with a hole between chamber 108 and battery portion 100A, which may house a fan 190 as described below. A temperature sensor 260 may also be included.

FIG. 12 further illustrates the embodiments of an electronic cigarette 10 provided in FIGS. 9-11 in accordance with the disclosure.

Referring now to FIG. 13, an embodiment of an electronic cigarette 10 including a battery portion 100B is provided. PCB 112 may include a microcontroller, voltage boost integrated circuit, accelerometer, and a Fan control circuitry. A fan 190, including blades and a motor, may be provided internally in battery segment 110 of battery portion 100B. Fan 190 may operate to facilitate air flow from external battery portion 100B, such as through one or more holes 152 provided in outer shell 106, through battery segment 110 and into cartomizer thereby establishing an air flow for inhalation in accordance with the disclosure. In some embodiments, fan 190 has a reversible operation in order to "clear" the air flow path in the event debris or excess vapor is caught in the air flow path. PCB 112 may also include one or more switches that, for instance, may be provided beneath control buttons, such as that exemplified in FIG. 15). PCB 112 may also include one or more LED's for these and other similar switch lights. PCB 112 may also operate to display a status message on an LED screen, which may be provided on outer shell 106 (e.g., as shown in FIG. 15). A status message may, for example, include messages to indicate a status of the electronic cigarette 10, such as when the cigarette 10 is activated, charging, or has reached a vaporization temperature. An LED screen may also display warning or error messages, for instance a danger message when a critical temperature has been detected by a sensor. Further, as illustrated in FIG. 14. In some embodiments, PCB 112 may operate to recognize the cartomizer 200/200A/200B/200C inserted into chamber 108, and in order to identify the vaporizable substance 300 included in cartomizer 200. For instance, PCB 112 may communicate with sensor 260 in cartomizer 200 in order to identify both the type and amount of vaporizable substance 300 within cartomizer 200. This identification may be included in the status message displayable on the LED screen on outer shell 106. Charger 400A may be utilized for charging battery 110 in battery portion 100C. It should be understood and appreciated that, in some embodiments, charger 400A may be inserted into chamber 108 of battery portions 100A/100B in addition to connection of charger 400A as described herein. It should be further understood and appreciated that in embodiments where charger 400/400A is coupled with battery portion 100 at a position other than where cartomizer 200 is connected, such as embodiments where charger 400A is coupled at or proximate to first end 102A, electronic cigarette 10 may operate with a pass through function, namely the ability to operate electronic cigarette 10 while the unit is charging from charger 400A.

FIG. 15 further illustrates the embodiments of an electronic cigarette 10 provided in FIGS. 13-14 in accordance with the disclosure.

Certain charger embodiments for rechargeable vaporizers or electronic cigarettes disclosed hereinabove, for example in FIG. 3, employ electrical contacts between the charger and the cartomizer portion's electrical connector. Under these circumstances, the cartomizer portion is first removed from the chamber to expose the electrical connector and thereafter a charger with compatible electrical contacts is inserted into the chamber. The invention contemplates other types and locations of connectors on the vaporizer and charger. Accordingly, in certain embodiments, the present invention provides a charger 400 for charging a vaporizer or electronic cigarette having charging contacts attached essentially transversely to its outer shell at an end distal to the cartomizer receiving portion and proximate to its battery portion. One such embodiment is shown in FIG. 14. In some of these embodiments where the cartomizer portion is not removed from the vaporizer to expose the electrical connector, the charging contacts are incorporated into the device such that the vaporizer or electronic cigarette may be operated in its typical fashion during the recharging of the battery ("pass-through" charging).

Figure 16:
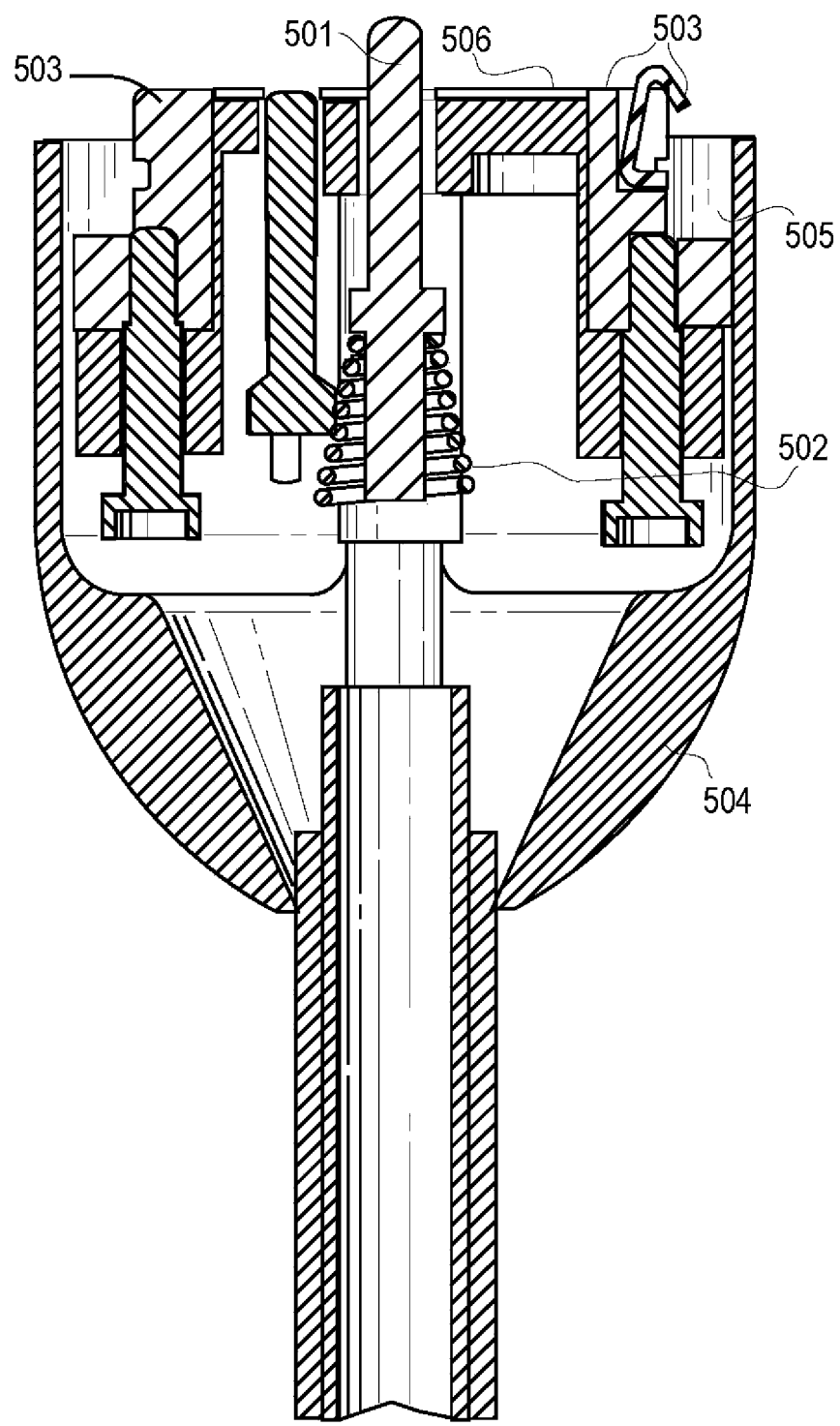
FIG. 16 illustrates a longitudinal cross sectional view of an embodiment of charger contacts on a power cord of a vaporizer or electronic cigarette charger of the present invention.
Figure 17:
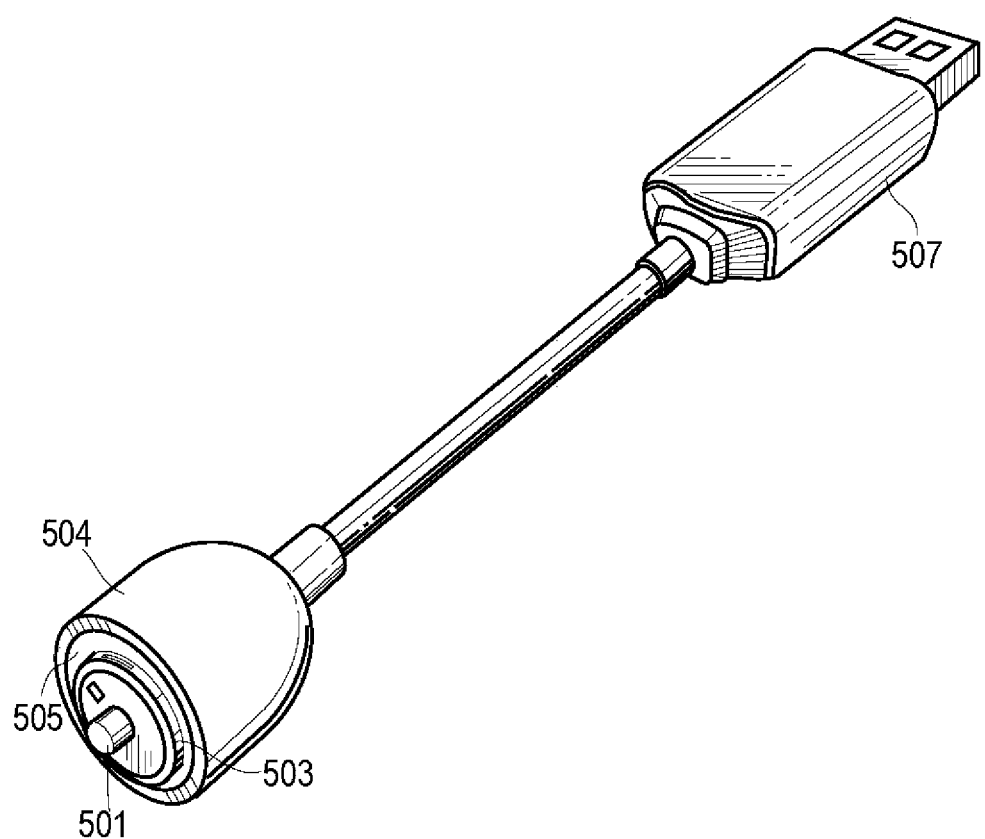
FIG. 17 illustrates a perspective view of an embodiment of charger contacts on a power cord of a vaporizer or electronic cigarette charger of the present invention.

Still other embodiments for chargers and rechargeable vaporizers or electronic cigarettes are illustrated in FIGS. 16, 17, 18, 19, and 20. For example, FIG. 16 depicts aspects of the portion of the charger that connects with the vaporizer during the charging operation. In this example, the positive connection to the vaporizer's charging contacts is facilitated through the use of a spring-loaded pogo pin (see 501 and 502). The negative connection pin (503) or other negative connection is isolated from the pogo pin by an insulator 506 to isolate the positive and negative connections from each other. At the contacts insulator surface such that it is isolated from electrical connections 501 and 503 is a wiper contact that is capable of powering a LED charging indicator light. In some instances the exterior housing 504 for the charger is at least in part, translucent or transparent, so that the indicator lamp can be readily observed. To maintain readily removable connectivity with the vaporizer, a magnet 505 is provided, and is typically in proximity to the outer edges of the charger's charging contacts and optionally takes the form of a ring disposed in substantially concentric fashion about the assembly containing the electrical contacts and insulation. The charger is generally held in the correct position for charging by magnetic attraction to the vaporizer's charging contacts. The magnetic attraction strength is such that the charger can be easily detached by just pulling on the charger. This level of attractive force may also allow the charger to break away if it is pulled too far away from the battery portion of the vaporizer so that no significant damage will occur to the vaporizer or the charger. Other aspects of the charger include one or more of support pieces and/or fixing screws, for example. The materials employed in the construction of the charger would be readily understood by the ordinarily skilled artisan once equipped with the teachings of the present invention. Any material that conducts electricity will generally be acceptable where transfer of electricity to charge the battery is required. Similarly, where insulation is a necessary property for normal operation, electrically non-conductive materials are typically acceptable. FIG. 17 illustrating a perspective drawing of a charger that employs a USB terminus connection 507 as a source of power for the charging operation. At the end distal to the USB terminus are the charger's charging contacts for the vaporizer or electronic cigarette, including a pogo pin-type positive connection 501, an insulator 506, a negative connection 503, a magnet 505 and a housing 504.

Figure 18:
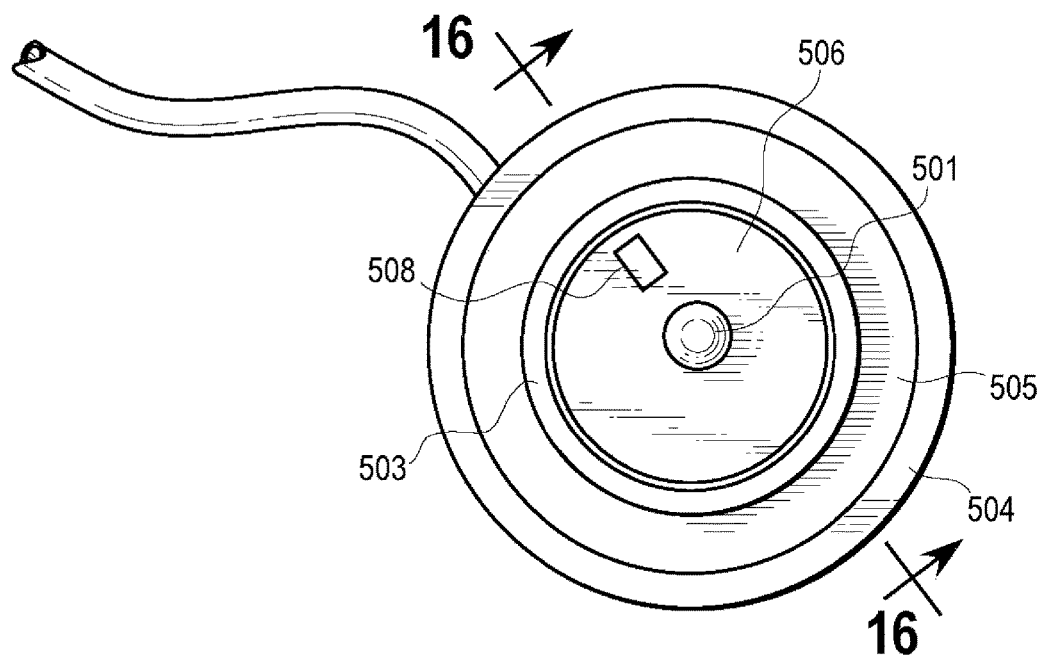
FIG. 18 illustrates a lateral view of an embodiment of charger contacts on a power cord of a vaporizer or electronic cigarette charger of the present invention.

FIG. 18 shows an alternate end on view of a charger's electrical contacts region, depicting a housing 504, magnet 505, negative connection 503, wiper contact 508 for an optional LED-type charging indicator light disposed on the housing, pogo pin-type positive connection 501, and insulator 506.

Figure 19:
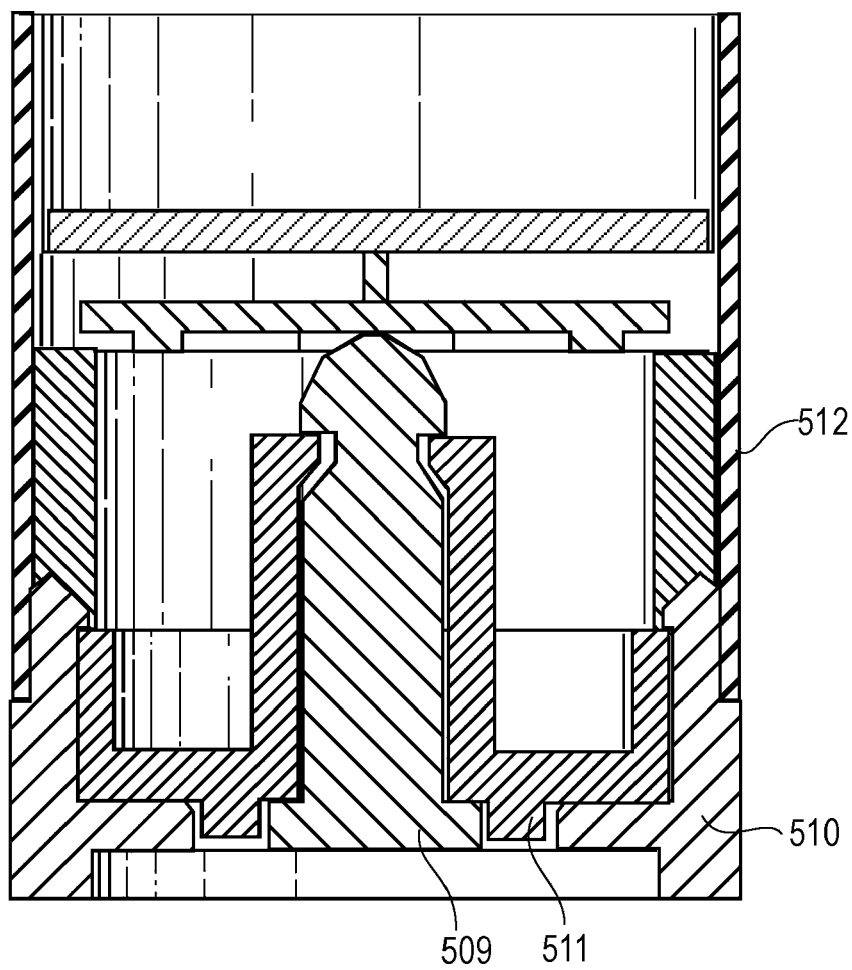
FIG. 19 illustrates a longitudinal cross sectional view of an embodiment of charger contacts of a vaporizer or electronic cigarette for connecting with a vaporizer or electronic cigarette charger of the present invention.

FIG. 19 illustrates a partial longitudinal cross section view of an embodiment of the vaporizer's electrical connector attached essentially transversely to its outer shell 512 at an end distal to the cartomizer receiving portion and proximate to its battery portion, which may be contacted with the chargers contacts illustrated in FIG. 18. FIG. 19 shows an arrangement of components for an embodiment of present invention's electrical connector including a positive contact 509, negative contact 510, and insulation 511.

Figure 20:
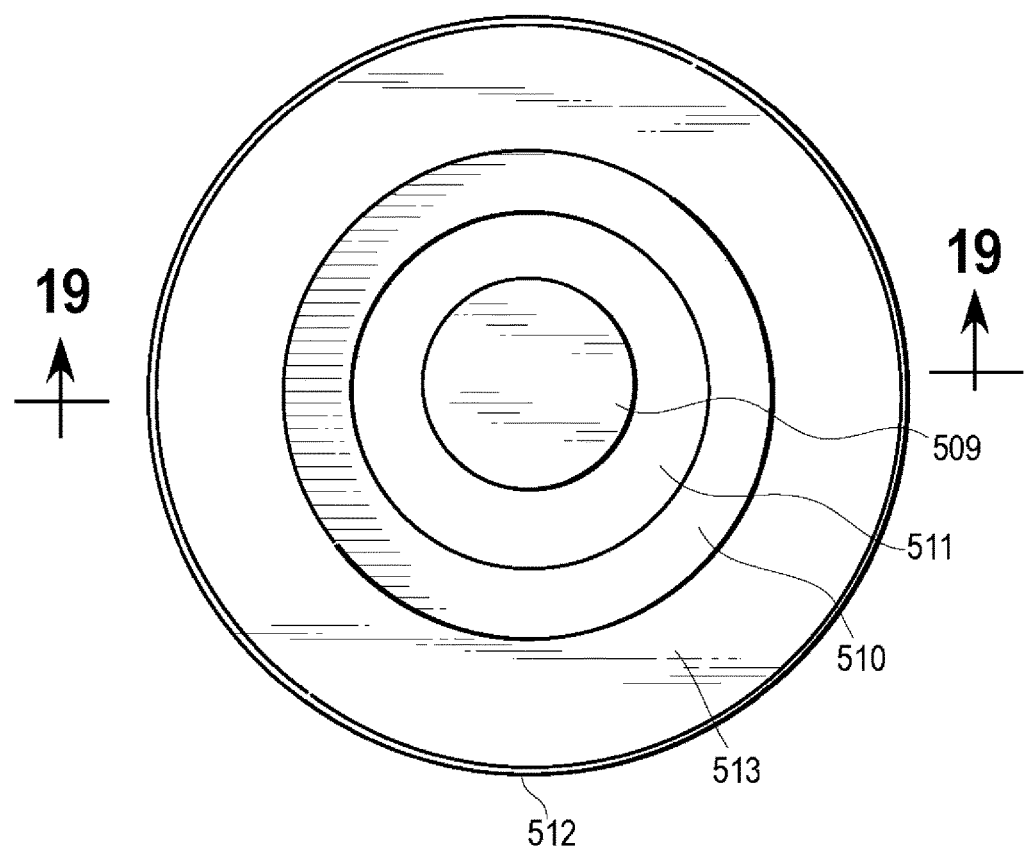
FIG. 20 illustrates a lateral cross sectional view of an embodiment of charger contacts on a vaporizer or electronic cigarette for connecting with a vaporizer or electronic cigarette charger of the present invention.

An alternative vaporizer electrical connector compatible with the charger shown in FIG. 18 is shown in FIG. 20 in an end on view. In this view, the positive contact 509 forms an innermost circle, surrounded by concentric circles of independently varying dimensions including an insulator 511, a negative contact 510, a magnet 513 and outer shell 512. In certain embodiments 513 may be a magnet or a magnetic material. In embodiments where 513 is a magnetic material, it is preferably magnetic metal, more preferably a ferromagnetic metal. The magnetic attraction between 513 and the magnet in the charger contacts is strong enough to hold the charger contacts and vaporizer charging contacts sufficiently so that the battery may be recharged. In certain preferred embodiments, the attraction is sufficiently strong to maintain the charger/vaporizer connection, but weak enough to be disconnected without substantial damage to the charger or the vaporizer.

Figure 21:
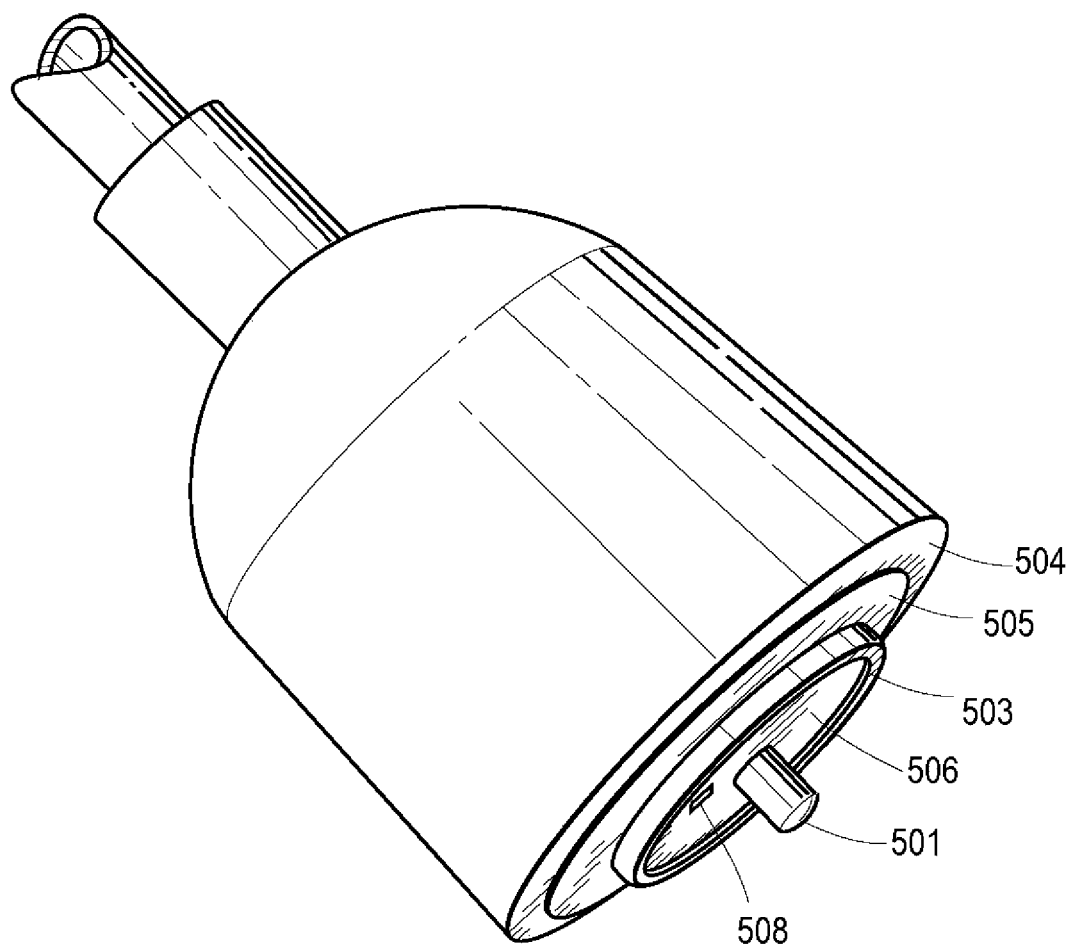
FIG. 21 illustrates a perspective view of an embodiment of charger contacts on a power cord of a vaporizer or electronic cigarette charger of the present invention.

FIG. 21 shows a perspective side on view of the FIG. 18 charger's electrical contacts region depicting a housing (504), magnet (505), negative connection (503), wiper contact (508), pogo pin-type positive connection (501), and insulator (506).

Figure 22:
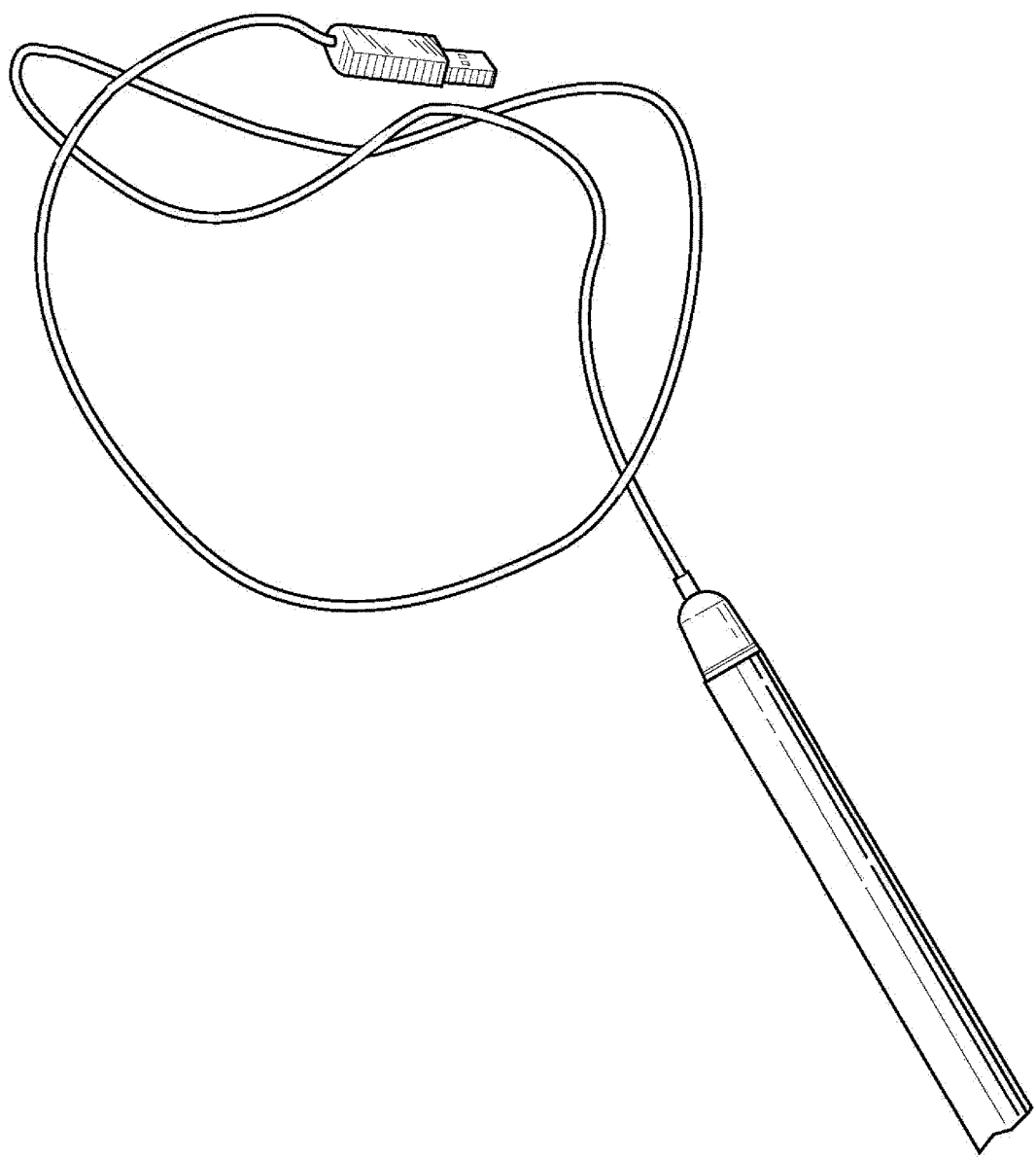
FIG. 22 illustrates a side view of an embodiment of a charger of the present invention in contact with charger contacts of a vaporizer or electronic cigarette for charging a vaporizer or electronic cigarette battery.

FIG. 22 shows the charger of FIG. 18 connected for recharging to the electrical connector of the vaporizer compatible with the charger shown in FIG. 20.

Vaporizer or electronic cigarette charger kits useful in, for example, the recharging of batteries used to power the vaporization process in such devices, are also within the ambit of the present invention. These kits typically include one or more chargers of the present invention, or alternatively a charger with multiple interchangeable power connectors (e.g., wall plug and USB connector). Such kits may further include, if desired, one or more of various compatible vaporizers or electronic cigarettes, their components, such as for example, one or more interchangeable cartomizers, cartomizer refills, etc., as will be readily apparent to those skilled in the art. Instructions, either as inserts or as labels, indicating quantities of the components contained in the kit, guidelines for operation or use, and/or guidelines for connecting any of the components and/or refilling the cartomizers, may also be included in the kit.

In accordance with certain embodiments of the present invention, there are provided methods which comprise contacting a charger of the present invention with a compatible vaporizer or electronic cigarette for a time and under conditions effective to recharge a rechargeable battery contained within said vaporizer or electronic cigarette sufficient to repower vaporizer or electronic cigarette for its continued use.

As will be understood by the ordinarily skilled artisan equipped with the disclosure herein, electrical contacts compatible with the charger must be provided for on or within the vaporizer or electronic cigarette.

The descriptions set forth above are meant to be illustrative and not limiting, and persons of skill in the art will recognize that various common and known deviations from the above described structures are considered to be within the scope of the disclosed concepts described herein.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

LIST OF REFERENCES

10 Electronic Cigarette
100 Battery Portion
100A Battery Portion
100B Battery Portion
102 Battery Housing Segment
102A First end of Battery Portion
104 Cartomizer Receiving Segment
104A Second end of Battery Portion
106 Shell
108 Cartomizer Chamber
110 Battery
112 PCB
112A PCB
114 Indicator
116 Ring Indicator
118 Button
118A Switch
120 Electrical Connector
122 Pin
124 Magnet
126 Protrusion
130 Window
152 Hole
160 Charging Contact
162 Magnet
190 Fan
200 Cartomizer
200A Cartomizer
200B Cartomizer
200C Cartomizer
202 Magnet
204 Groove
208 Body
210 Insertion End
212 Mouthpiece End
214 Heating Element
214A Heating Element
214B Basin
216 Wick
218 Electrical Contact
220 Mouthpiece
222 Inhalation Tube
224 Threading
226 Bushing
228 Colored Ring
240 Container
242 Insulating Material
250 Screen
252 Hole
260 Sensor
262 Cartomizer PCB
300 Vaporizable Substance
300A Vaporizable Fluid
300B Vaporizable Dry Substance
300C Vaporizable Wax
400 Charger
400A Charger
402 Electrical Contact
404 Magnet
410 Plug
420 Light
501 pogo pin
502 spring
503 negative connection pin
504 exterior housing
505 magnet
506 insulator
507 USB terminus connection
508 wiper contact
509 positive contact
510 negative contact
511 insulation
512 outer shell
513 magnet or magnetic metal

What is claimed:

1. A vaporizer comprising:
a shell having a battery segment and a cartomizer receiving segment, the cartomizer receiving segment defining a chamber having an insertion end distal from the battery segment and a base end proximate to the battery segment;
a cartomizer insertable into the chamber at the insertion end, the cartomizer including:
an outer cartomizer shell,
a holding structure provided within, and secured to, the outer cartomizer shell, the holding structure including a basin dimensioned to hold a vaporizable substance,
a heating element provided within the basin operable to heat the vaporizable substance,
cartomizer electrical contacts provided on the exterior of the cartomizer,
cartomizer electrical circuitry operable to direct an electronic current between the cartomizer electrical contacts and the heating element, and
a mouthpiece fluidly communicable with the basin, the mouthpiece extending from the insertion end of the chamber when the cartomizer is inserted in the chamber,
wherein the heating element is activated by the current and is operable to heat the vaporizable substance to a vaporization temperature;
a battery housed within the battery segment;
battery electrical contacts provided between the base end of the chamber and the battery segment, the battery electrical contacts positioned to contact the cartomizer electrical contacts when the cartomizer is inserted in the chamber; and
battery electrical circuitry housed within the battery segment and operable to direct an electrical current between the battery, the battery electrical contacts, the cartomizer electrical contacts, the heating element, and the inserted cartomizer.

2. The vaporizer of claim 1, further comprising a container having container walls provided proximate to the basin, the container dimensioned such that the vaporizable substance may pass from the container to the basin.

3. The vaporizer of claim 1, wherein the holding structure further includes a stabilizing element connectable with the outer cartomizer shell, the basin secured to the stabilizing element.

4. The vaporizer of claim 3, wherein the stabilizing element includes a first threaded portion threadably connectable with the outer cartomizer shell.

5. The vaporizer of claim 4, further comprising a container including container walls and a threaded container portion, the container dimensioned such that the vaporizable substance is passable from between the container walls to the basin, and
the stabilizing element includes a second threaded portion threadably engagable with the threaded container portion.

6. The vaporizer of claim 5, further comprising at least one air passage provided through at least one hole in the outer shell and at least one hole in the container wall.

7. The vaporizer of claim 6, wherein the vaporizable substance is a wax.

8. The vaporizer of claim 6, further comprising a cartomizer printed circuit board in electronic communication with the cartomizer electrical circuitry.

9. The vaporizer of claim 1, further comprising a container having container walls provided proximate to the basin, the container arranged relative to the basin such that the vaporizable substance may pass from the container into the basin.

10. The vaporizer of claim 9, wherein the basin defines a cavity and includes a barrier that covers the cavity.

11. The vaporizer of claim 10, wherein the container is arranged relative to the basin such that the vaporizable substance may pass from the container into the basin by passing through the barrier.

12. The vaporizer of claim 10, wherein the barrier comprises a screen or mesh.

* * * * *